(12) United States Patent
Al-Ali et al.

(10) Patent No.: US 12,383,194 B2
(45) Date of Patent: Aug. 12, 2025

(54) DEPTH OF CONSCIOUSNESS MONITOR

(71) Applicant: Masimo Corporation, Irvine, CA (US)

(72) Inventors: Ammar Al-Ali, San Juan Capistrano, CA (US); Walter M. Weber, Laguna Hills, CA (US); Faisal Kashif, Irvine, CA (US); Mohammad Usman, Mission Viejo, CA (US); Balaji Chandrasekaran, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 46 days.

(21) Appl. No.: 16/752,303

(22) Filed: Jan. 24, 2020

(65) Prior Publication Data

US 2020/0229729 A1    Jul. 23, 2020

Related U.S. Application Data

(62) Division of application No. 13/911,939, filed on Jun. 6, 2013, now Pat. No. 10,542,903.

(60) Provisional application No. 61/703,747, filed on Sep. 20, 2012, provisional application No. 61/656,974, filed on Jun. 7, 2012.

(51) Int. Cl.
| | |
|---|---|
| *A61B 5/00* | (2006.01) |
| *A61B 5/372* | (2021.01) |
| *A61B 5/389* | (2021.01) |
| *A61M 5/172* | (2006.01) |

(52) U.S. Cl.
CPC ............ *A61B 5/4821* (2013.01); *A61B 5/372* (2021.01); *A61B 5/389* (2021.01); *A61B 5/4839* (2013.01); *A61M 5/1723* (2013.01); *A61M 2205/35* (2013.01); *A61M 2205/502* (2013.01); *A61M 2230/04* (2013.01)

(58) Field of Classification Search
None
See application file for complete search history.

(56) References Cited

U.S. PATENT DOCUMENTS

| | | |
|---|---|---|
| 3,702,431 A | 11/1972 | Pinckaers |
| 3,710,041 A | 1/1973 | Hayashi et al. |
| 3,719,830 A | 3/1973 | Ananiades |
| 4,610,259 A | 9/1986 | Cohen et al. |
| 4,960,128 A | 10/1990 | Gordon et al. |
| 4,964,408 A | 10/1990 | Hink et al. |

(Continued)

FOREIGN PATENT DOCUMENTS

| | | |
|---|---|---|
| EP | 1 741 388 | 1/2007 |
| WO | WO 02/032305 | 4/2002 |
| WO | WO 2013/184965 | 12/2013 |

OTHER PUBLICATIONS

US 2024/0016391 A1, 01/2024, Lapotko et al. (withdrawn)

(Continued)

*Primary Examiner* — Anh Tuan T Nguyen
*Assistant Examiner* — Jae Woo
(74) *Attorney, Agent, or Firm* — Knobbe, Martens, Olson & Bear, LLP

(57) ABSTRACT

The present disclosure relates to physiological monitoring to determine the depth of consciousness of a patient under sedation. The monitor includes an EEG sensor and a depth of consciousness monitor. The depth of consciousness monitor can utilize treatment data, such as patient data and/or drug profile information with an EEG signal to determine whether the patient is adequately sedated.

8 Claims, 15 Drawing Sheets

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,699,808 A * | 12/1997 | John .................. A61B 5/4821 |
| | | 600/483 |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,016,444 A | 1/2000 | John |
| 6,016,449 A | 1/2000 | Fischell et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,366,805 B1 | 4/2002 | Lutz |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,654,626 B2 | 11/2003 | Devlin et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,164 B1 | 2/2004 | Babayoff et al. |
| 6,697,656 B1 | 2/2004 | Al-Ali |
| 6,697,657 B1 | 2/2004 | Shehada et al. |
| 6,697,658 B2 | 2/2004 | Al-Ali |

(56) References Cited

U.S. PATENT DOCUMENTS

| | | |
|---|---|---|
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,944,501 B1 | 9/2005 | Pless |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,047,054 B2 | 5/2006 | Benni |
| 7,048,687 B1 | 5/2006 | Reuss et al. |
| 7,067,893 B2 | 6/2006 | Mills et al. |
| 7,072,701 B2 | 7/2006 | Chen et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,550 B1 | 10/2007 | Rosenboom |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,308,894 B2 | 12/2007 | Hickle |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,341,599 B1 | 3/2008 | Peyman |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfire et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |

(56) References Cited

U.S. PATENT DOCUMENTS

| | | |
|---|---|---|
| 7,761,146 B2 | 7/2010 | Carlson et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |

(56) References Cited

U.S. PATENT DOCUMENTS

| | | |
|---|---|---|
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,330 B2 | 11/2015 | Lin |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |

(56) References Cited

U.S. PATENT DOCUMENTS

| | | |
|---|---|---|
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,712,318 B2 | 7/2017 | Foerester et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Al-Ali et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |

(56) References Cited

U.S. PATENT DOCUMENTS

| | | |
|---|---|---|
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| D1,031,729 S | 6/2024 | Forrest et al. |
| 12,004,869 B2 | 6/2024 | Kiani et al. |
| 12,014,328 B2 | 6/2024 | Wachman et al. |
| D1,036,293 S | 7/2024 | Al-Ali et al. |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| 12,066,426 B1 | 8/2024 | Lapotko et al. |
| D1,041,511 S | 9/2024 | Indorf et al. |
| D1,042,596 S | 9/2024 | DeJong et al. |
| D1,042,852 S | 9/2024 | Hwang |
| 12,076,159 B2 | 9/2024 | Belur Nagaraj et al. |
| 12,082,926 B2 | 9/2024 | Sharma et al. |
| D1,044,828 S | 10/2024 | Chandran et al. |
| D1,048,571 S | 10/2024 | Yu et al. |
| D1,048,908 S | 10/2024 | Al-Ali et al. |
| 12,106,752 B2 | 10/2024 | Campbell et al. |
| 12,114,974 B2 | 10/2024 | Al-Ali et al. |
| 12,126,683 B2 | 10/2024 | Koo et al. |
| 12,127,838 B2 | 10/2024 | Olsen et al. |
| 12,128,213 B2 | 10/2024 | Kiani et al. |
| 12,131,661 B2 | 10/2024 | Pauley et al. |
| D1,050,910 S | 11/2024 | Al-Ali et al. |
| 12,178,572 B1 | 12/2024 | Pauley et al. |
| 12,178,581 B2 | 12/2024 | Telfort et al. |
| 12,178,852 B2 | 12/2024 | Kiani et al. |
| D1,057,159 S | 1/2025 | DeJong et al. |
| D1,057,160 S | 1/2025 | DeJong et al. |
| 12,198,790 B1 | 1/2025 | Al-Ali |
| 12,200,421 B2 | 1/2025 | Campbell et al. |
| 12,207,901 B1 | 1/2025 | Lapotko et al. |
| D1,060,680 S | 2/2025 | Al-Ali et al. |
| D1,063,893 S | 2/2025 | DeJong et al. |
| 12,235,941 B2 | 2/2025 | Kiani et al. |
| 12,236,767 B2 | 2/2025 | Muhsin |

(56) References Cited

U.S. PATENT DOCUMENTS

| | | | |
|---|---|---|---|
| D1,066,244 S | 3/2025 | Lim et al. | |
| D1,066,672 S | 3/2025 | Al-Ali et al. | |
| 2001/0034477 A1 | 10/2001 | Mansfield et al. | |
| 2001/0039483 A1 | 11/2001 | Brand et al. | |
| 2002/0010401 A1 | 1/2002 | Bushmakin et al. | |
| 2002/0058864 A1 | 5/2002 | Mansfield et al. | |
| 2002/0059159 A1* | 5/2002 | Cook | A61B 5/4094 706/62 |
| 2002/0117176 A1* | 8/2002 | Mantzaridis | A61B 5/1106 128/204.23 |
| 2002/0133080 A1 | 9/2002 | Apruzzese et al. | |
| 2002/0173729 A1* | 11/2002 | Viertio-Oja | A61B 5/374 600/544 |
| 2003/0013975 A1 | 1/2003 | Kiani | |
| 2003/0018243 A1 | 1/2003 | Gerhardt et al. | |
| 2003/0055355 A1* | 3/2003 | Viertio-Oja | A61B 5/16 600/544 |
| 2003/0144582 A1 | 7/2003 | Cohen et al. | |
| 2003/0145854 A1* | 8/2003 | Hickle | G16H 40/63 128/204.18 |
| 2003/0156288 A1 | 8/2003 | Barnum et al. | |
| 2003/0212312 A1 | 11/2003 | Coffin, IV et al. | |
| 2004/0038169 A1 | 2/2004 | Mandelkern et al. | |
| 2004/0073415 A1* | 4/2004 | Farhat | G06N 3/02 703/2 |
| 2004/0106163 A1 | 6/2004 | Workman, Jr. et al. | |
| 2004/0193068 A1* | 9/2004 | Burton | A61B 5/4812 600/544 |
| 2005/0007091 A1* | 1/2005 | Makeig | A61B 5/374 324/76.13 |
| 2005/0010116 A1* | 1/2005 | Korhonen | A61B 5/4035 600/481 |
| 2005/0055276 A1 | 3/2005 | Kiani et al. | |
| 2005/0124863 A1* | 6/2005 | Cook | A61B 5/4094 600/300 |
| 2005/0124888 A1* | 6/2005 | Jjt Rein | A61B 8/0833 600/443 |
| 2005/0234317 A1 | 10/2005 | Kiani | |
| 2006/0062432 A1* | 3/2006 | Watanabe | G08G 1/163 382/104 |
| 2006/0073719 A1 | 4/2006 | Kiani | |
| 2006/0149160 A1* | 7/2006 | Kofol | A61B 5/369 600/544 |
| 2006/0161054 A1 | 7/2006 | Reuss et al. | |
| 2006/0189871 A1 | 8/2006 | Al-Ali et al. | |
| 2007/0010756 A1* | 1/2007 | Viertio-Oja | G16H 50/50 600/544 |
| 2007/0055114 A1* | 3/2007 | Viertio-Oja | A61B 5/389 600/300 |
| 2007/0073116 A1 | 3/2007 | Kiani et al. | |
| 2007/0116119 A1* | 5/2007 | Wang | H04N 19/51 375/240.12 |
| 2007/0150025 A1* | 6/2007 | Dilorenzo | A61B 5/4094 607/45 |
| 2007/0180140 A1 | 8/2007 | Welch et al. | |
| 2007/0208322 A1 | 9/2007 | Rantala et al. | |
| 2007/0244377 A1 | 10/2007 | Cozad et al. | |
| 2007/0282478 A1 | 12/2007 | Al-Ali et al. | |
| 2008/0064965 A1 | 3/2008 | Jay et al. | |
| 2008/0094228 A1 | 4/2008 | Welch et al. | |
| 2008/0103375 A1 | 5/2008 | Kiani | |
| 2008/0107307 A1* | 5/2008 | Altherr | H04N 5/23248 382/107 |
| 2008/0117968 A1* | 5/2008 | Wang | H04N 19/61 375/240.12 |
| 2008/0204566 A1* | 8/2008 | Yamazaki | G03B 5/00 348/208.99 |
| 2008/0221418 A1 | 9/2008 | Al-Ali et al. | |
| 2008/0234598 A1* | 9/2008 | Snyder | A61B 5/374 600/545 |
| 2009/0036759 A1 | 2/2009 | Ault et al. | |
| 2009/0093687 A1* | 4/2009 | Telfort | A61B 5/318 600/300 |
| 2009/0095926 A1 | 4/2009 | MacNeish, III | |
| 2009/0131762 A1 | 5/2009 | Pelzek et al. | |
| 2009/0149148 A1* | 6/2009 | Kurtz | G06K 9/00536 455/307 |
| 2009/0160642 A1 | 6/2009 | Kim | |
| 2009/0198145 A1* | 8/2009 | Chow | A61K 31/137 514/1.1 |
| 2009/0247984 A1 | 10/2009 | Lamego et al. | |
| 2009/0275813 A1 | 11/2009 | Davis | |
| 2009/0275844 A1 | 11/2009 | Al-Ali | |
| 2009/0322865 A1* | 12/2009 | Wang | A61B 5/14539 348/68 |
| 2010/0004518 A1 | 1/2010 | Vo et al. | |
| 2010/0030040 A1 | 2/2010 | Poeze et al. | |
| 2010/0099964 A1 | 4/2010 | O'Reilly et al. | |
| 2010/0220180 A1* | 9/2010 | Lee | A61B 5/073 348/74 |
| 2010/0234718 A1 | 9/2010 | Sampath et al. | |
| 2010/0270257 A1 | 10/2010 | Wachman et al. | |
| 2010/0324441 A1 | 12/2010 | Hargrove et al. | |
| 2011/0028806 A1 | 2/2011 | Merritt et al. | |
| 2011/0028809 A1 | 2/2011 | Goodman | |
| 2011/0040197 A1 | 2/2011 | Welch et al. | |
| 2011/0054272 A1 | 3/2011 | Derchak | |
| 2011/0082711 A1 | 4/2011 | Poeze et al. | |
| 2011/0087081 A1 | 4/2011 | Kiani et al. | |
| 2011/0116547 A1* | 5/2011 | Chen | G06T 3/40 375/240.16 |
| 2011/0118561 A1 | 5/2011 | Tari et al. | |
| 2011/0125060 A1* | 5/2011 | Telfort | A61B 7/003 600/586 |
| 2011/0137297 A1 | 6/2011 | Kiani et al. | |
| 2011/0172498 A1 | 7/2011 | Olsen et al. | |
| 2011/0184307 A1 | 7/2011 | Hulin | |
| 2011/0208015 A1 | 8/2011 | Welch et al. | |
| 2011/0230733 A1 | 9/2011 | Al-Ali | |
| 2011/0270047 A1 | 11/2011 | O'Brien | |
| 2012/0044347 A1* | 2/2012 | Sugio | H04N 5/23296 348/135 |
| 2012/0053433 A1 | 3/2012 | Chamoun et al. | |
| 2012/0083673 A1 | 4/2012 | Al-Ali et al. | |
| 2012/0123231 A1 | 5/2012 | O'Reilly | |
| 2012/0165629 A1 | 6/2012 | Merritt et al. | |
| 2012/0203079 A1* | 8/2012 | McLaughlin | A61B 5/4094 600/301 |
| 2012/0203087 A1* | 8/2012 | McKenna | A61B 5/4821 600/322 |
| 2012/0209082 A1 | 8/2012 | Al-Ali | |
| 2012/0209084 A1 | 8/2012 | Olsen et al. | |
| 2012/0226117 A1 | 9/2012 | Lamego et al. | |
| 2012/0277548 A1* | 11/2012 | Burton | A61B 5/02405 600/301 |
| 2012/0283524 A1 | 11/2012 | Kiani et al. | |
| 2013/0023775 A1 | 1/2013 | Lamego et al. | |
| 2013/0041591 A1 | 2/2013 | Lamego | |
| 2013/0060147 A1 | 3/2013 | Welch et al. | |
| 2013/0096405 A1 | 4/2013 | Garfio | |
| 2013/0096936 A1 | 4/2013 | Sampath et al. | |
| 2013/0150748 A1 | 6/2013 | Jensen | |
| 2013/0197339 A1* | 8/2013 | Bardakjian | A61B 5/291 600/383 |
| 2013/0243021 A1 | 9/2013 | Siskavich | |
| 2013/0253334 A1 | 9/2013 | Al-Ali et al. | |
| 2013/0276785 A1 | 10/2013 | Melker et al. | |
| 2013/0296672 A1 | 11/2013 | O'Neil et al. | |
| 2013/0296713 A1 | 11/2013 | Al-Ali et al. | |
| 2013/0324808 A1 | 12/2013 | Al-Ali et al. | |
| 2013/0331660 A1 | 12/2013 | Al-Ali et al. | |
| 2013/0345921 A1 | 12/2013 | Al-Ali et al. | |
| 2014/0012100 A1 | 1/2014 | Al-Ali et al. | |
| 2014/0051953 A1 | 2/2014 | Lamego et al. | |
| 2014/0120564 A1 | 5/2014 | Workman et al. | |
| 2014/0121482 A1 | 5/2014 | Merritt et al. | |
| 2014/0127137 A1 | 5/2014 | Bellott et al. | |
| 2014/0163344 A1 | 6/2014 | Al-Ali | |
| 2014/0166076 A1 | 6/2014 | Kiani et al. | |
| 2014/0171763 A1 | 6/2014 | Diab | |
| 2014/0180038 A1 | 6/2014 | Kiani | |

(56) References Cited

U.S. PATENT DOCUMENTS

| | | |
|---|---|---|
| 2014/0180154 A1 | 6/2014 | Sierra et al. |
| 2014/0180160 A1 | 6/2014 | Brown et al. |
| 2014/0187973 A1* | 7/2014 | Brown .................. G16H 50/20 600/483 |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0142082 A1 | 5/2015 | Simon et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272508 A1 | 10/2015 | Chiouchang et al. |
| 2015/0272514 A1 | 10/2015 | Kiani et al. |
| 2015/0306390 A1* | 10/2015 | Zalay ................. A61N 1/36064 607/45 |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287162 A1* | 10/2016 | Bardakjian ............ A61B 5/291 |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324446 A1* | 11/2016 | Prerau ................. A61B 5/0533 |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0181693 A1 | 6/2017 | Kim et al. |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |

(56) References Cited

U.S. PATENT DOCUMENTS

| | | |
|---|---|---|
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0320988 A1 | 10/2019 | Ahmed et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0041953 A1* | 2/2021 | Poltorak ............ A61B 5/0077 |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0260894 A1 | 8/2024 | Olsen |
| 2024/0267698 A1 | 8/2024 | Telfort et al. |

(56) References Cited

U.S. PATENT DOCUMENTS

| | | |
|---|---|---|
| 2024/0277233 A1 | 8/2024 | Al-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |
| 2024/0380246 A1 | 11/2024 | Moran |
| 2024/0380247 A1 | 11/2024 | Moran |
| 2024/0404549 A1 | 12/2024 | Campbell et al. |
| 2025/0000458 A1 | 1/2025 | Abdul-Hafiz et al. |

OTHER PUBLICATIONS

Ionescu et al., C. M., Variable Time-Delay Estimation for Anesthesia Control During Intensive Care, IEEE Transactions on Biomedical Engineering, Feb. 1, 2011, pp. 363-369, vol. 58, No. 2, IEEE Service Center, Piscataway, NJ, USA.

International Search Report and Written Opinion received in PCT Application No. PCT/US2013/044598, dated Sep. 25, 2013.

Letter from Tara A. Ryan to Masimo Corporation re 510(k) No. K172890, U.S. Food & Drug Administration, dated Jan. 26, 2018 in 9 pages.

Letter from Todd D. Courtney to Masimo Corporation re 510(k) No. K203113, U.S. Food & Drug Administration, dated Feb. 25, 2022.

\* cited by examiner

DEPTH OF CONSCIOUSNESS MONITOR

CROSS REFERENCE TO RELATED APPLICATIONS

This application is a divisional of U.S. application Ser. No. 13/911,939, filed Jun. 6, 2013, now U.S. Pat. No. 10,542,903, which claims the benefit of priority from U.S. Provisional No. 61/703,747, filed Sep. 20, 2012, and U.S. Provisional No. 61/656,974, filed Jun. 7, 2012, all of which are incorporated by reference in their entireties.

FIELD OF THE DISCLOSURE

The present disclosure relates to the field of patient monitoring. In some embodiments, the disclosure relates to monitoring the depth of consciousness of a patient under anesthetic sedation.

BACKGROUND

General anesthesia is often used to put patients to sleep and block pain and memory during medical or diagnostic procedures. While extremely useful, general anesthesia is not risk free. Caregivers therefore generally seek to maintain a depth of consciousness consistent with the needs of a particular medical procedure. Caregivers will monitor various physiological parameters of the patient to predict the patient's depth of consciousness. In response to monitored parameters, the caregiver may manually adjust the anesthetic dosage level to avoid over and under dosing. However, as a patient's depth of consciousness may frequently change, caregivers often employ a host of monitoring technologies to attempt to periodically, sporadically, or continually ascertain the wellness and consciousness of a patient. For example, caregivers may desire to monitor one or more of a patient's temperature, electroencephalogram or EEG, brain oxygen saturation, stimulus response, electromyography or EMG, respiration, body oxygen saturation or other blood analytes, pulse, hydration, blood pressure, perfusion, or other parameters or combinations of parameters. For many of the foregoing, monitoring technologies are individually readily available and widely used, such as, for example, pulse oximeters, vital signs monitors, and the like.

In their depth of consciousness monitoring, caregivers may also use recording devices to acquire EEG signals. For example, caregivers place electrodes on the skin of the forehead to detect electrical activity produced by the firing of neurons within the brain. From patterns in the electrical activity, caregivers attempt to determine, among other things, the state of consciousness of the brain. Caregivers may also use a pulse oximeter or cerebral oximetry to determine the percentage of oxygenation of the hemoglobin in the patient's blood. Caregivers may also use an EMG monitor to detect the muscular action and mechanical impulses generated by the musculature around the patient's forehead, among other bodily locations. Caregivers manually monitor such physiological parameters and then manually adjust anesthetic dosage.

However, manual monitoring and dosage adjustment could lead to serious adverse results, including death, if improperly performed. In addition, typical depth of consciousness monitors do not account for variations in responses to sedation therapies that exist between patient demographics. Furthermore, typical depth of consciousness monitors do not account for differences in physiological responses that exists between particular sedation therapies and among different patient populations. Therefore, there remains a need in the art for a depth of consciousness monitor that is configured to automatically communicate with a caregiver and/or an anesthetic dosage device to provide accurate control over patient care by accounting for variations between populations and drug actions.

SUMMARY

Based on at least the foregoing, the present disclosure seeks to overcome some or all of the drawbacks discussed above and provide additional advantages over prior technologies. The present disclosure describes embodiments of noninvasive methods, devices, and systems for monitoring depth of consciousness through brain electrical activity.

In one embodiment, a depth of consciousness monitor is configured to determine the level of sedation of a medical patient. The depth of consciousness monitor includes: an EEG interface configured to receive an EEG signal from an EEG sensor; an EEG front end configured to pre-process the EEG signal; a processor, configured to determine a level of sedation of a medical patient based at least upon the pre-processed EEG signal, wherein the processor is further configured to determine delay information associated with the time the EEG signal is received and the time the level of sedation is determined; and a drug delivery device interface, configured to provide the level of sedation and the delay information to a drug delivery device.

In some embodiments the EEG front end includes an EEG engine and an EMG engine configured to extract EEG information and EMG information from the EEG signal, respectively. In some embodiments, the processor is further configured to time stamp the EEG signal when received from the EEG sensor. In one embodiment, the depth of consciousness monitor also includes an additional sensor front end, such as an SpO2 sensor front end. In some embodiments, the depth of consciousness monitor also includes a data port configured to receive at least one of patient data and drug profile information. The processor may be configured to determine a level of sedation of a medical patient based at least upon the pre-processed EEG signal and the at least one of patient data and drug profile information. In some embodiments, the depth of consciousness monitor also includes the EEG sensor and/or the drug delivery system. In some embodiments, the drug delivery device interface includes a wireless communication device.

In another embodiment, a depth of consciousness monitor is configured to determine the level of sedation of a medical patient. The depth of consciousness monitor includes: an EEG interface configured to receive an EEG signal from an EEG sensor; an EEG front end configured to pre-process the EEG signal; a processor, configured to determine a level of sedation of a medical patient based at least upon the pre-processed EEG signal, and a data port configured to transmit the patient sedation level. The processor can include: two or more computing engines, each configured to compute a possible sedation level according to a different process; and a decision logic module, configured to determine the patient's sedation level based at least upon the possible sedation level computations;

In some embodiments, at least one of the computing engines is configured to implement a motion vector process, a phase coherence process, and/or utilize a brain model to compute one of the possible sedation levels. The EEG front end may include an EEG engine and an EMG engine configured to extract EEG information and EMG information from the EEG signal, respectively. In some embodiments, the data port comprises a display and/or a wireless communication device.

In yet another embodiment, a method of determining the level of sedation of a medical patient is provided. The method includes: receiving an EEG signal indicative of a medical patient's EEG; receiving treatment data associated with at least one of the medical patient and a drug to be delivered to the medical patient; and determining a level of sedation based at least upon the EEG signal and the treatment data.

In some embodiments, the treatment data includes at least one of a patient age, age classification, sex, weight, body-mass index, a physiological parameters, a temperature, a blood oxygen concentration, an EMG signal, a drug type, a drug class, a mechanism of delivery, and an active ingredient. In some embodiments, determining a level of sedation comprises determining two or more possible levels of sedation with parallel computing engines and wherein said determining the level of sedation of the medical patient is based upon said possible levels of sedation. In some embodiments, determining the level of sedation comprises averaging two or more possible levels of sedation and/or selecting one of the possible levels of sedation as the level of sedation of the medical patient. In some embodiments, determining the possible levels of sedation is performed with motion vector analysis, phase coherence, and or by utilizing a brain model.

For purposes of summarizing the disclosure, certain aspects, advantages and novel features of the disclosure have been described herein. Of course, it is to be understood that not necessarily all such aspects, advantages or features will be embodied in any particular embodiment of the disclosure.

BRIEF DESCRIPTION OF THE DRAWINGS

The following drawings and the associated descriptions are provided to illustrate embodiments of the present disclosure and do not limit the scope of the claims.

DETAILED DESCRIPTION

Figure 1:
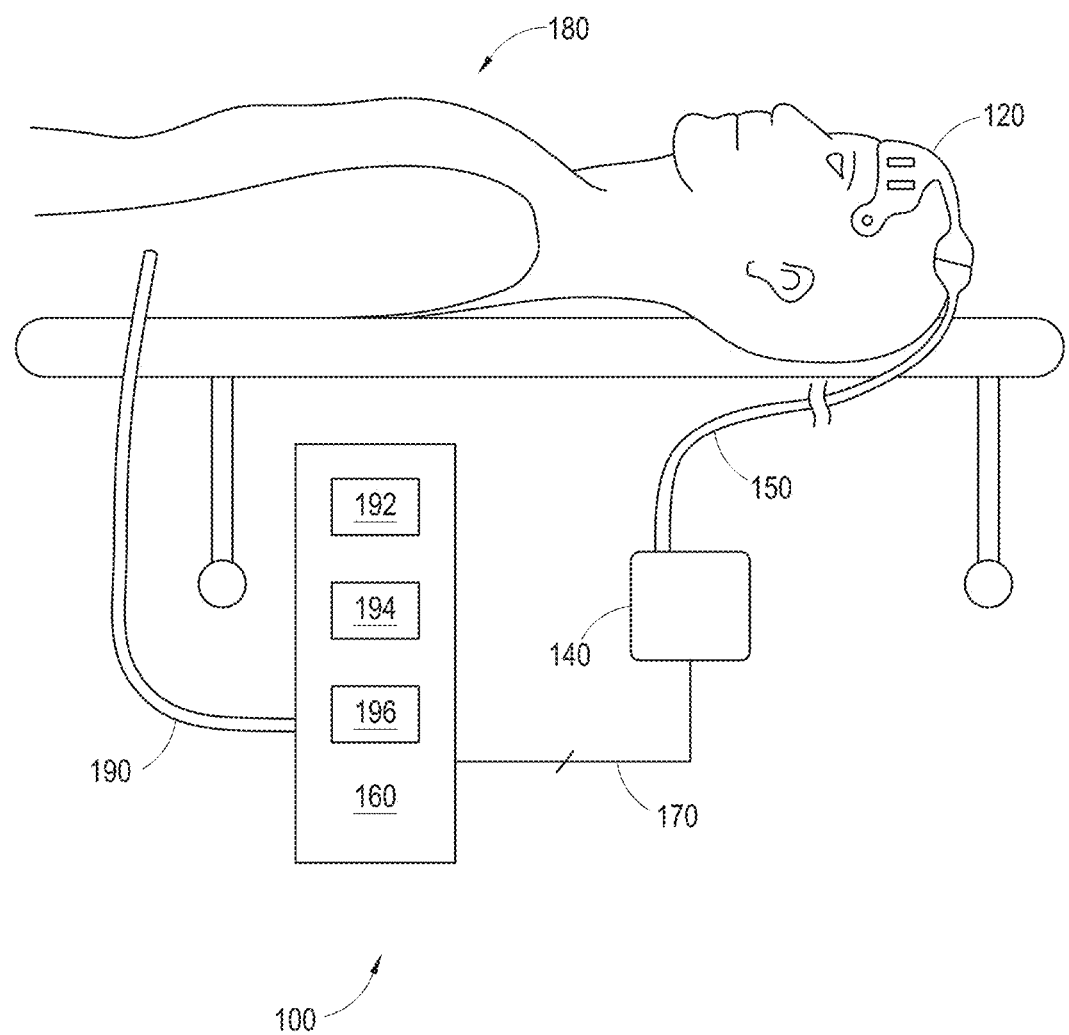
FIG. 1 illustrates an embodiment of a depth of consciousness monitoring system under closed-loop control.

The present disclosure generally relates to patient monitoring devices. In order to provide a complete and accurate assessment of the state of a patient's various physiological systems, in an embodiment, a sensor may advantageously monitor one, multiple or combinations of EEG, EMG, cerebral oximetry, temperature, pulse oximetry, respiration, and other physiological parameters. In various embodiments, the sensor includes a disposable portion and reusable portion. For example, the disposable portion may advantageously include components near a measurement site surface (the patient's skin), including, for example, an EEG sensor, an EMG sensor, a temperature sensor, tape, adhesive elements, positioning elements, or the like. In addition, or alternatively, the reusable portion may advantageously include other components, circuitry or electronics, which, in some embodiments include time-of-use restrictions for quality control or the like. The reusable portion, can be used multiple times for a single patient, across different patients, or the like, often depending upon the effectiveness of sterilization procedures. The reusable components may include, for example, cerebral oximetry components, pulse oximetry components and other components to measure other various parameters.

In an embodiment, the disposable portion of the sensor may include an inductance connection or other electrical connection to the reusable portion of the sensor. The physiological signals from all sensors can be transmitted through a common cable to a depth of consciousness monitor. In an embodiment, the depth of consciousness monitor may include an analog to digital converter, various electrical filters, and a microcontroller for processing and controlling the various sensor components.

In an embodiment, a depth of consciousness monitor is configured to communicate with the forehead sensor and one or more host display and patient monitoring stations. In an embodiment, the patient monitoring station may be a pulse oximeter. In an embodiment, the pulse oximeter may perform integrated display, data monitoring and processing of patient parameters including a connection for power and data communication. In an embodiment, some or all communication may be through wired, wireless, or other electrical connections. In an embodiment, the depth of consciousness monitor may advantageously be housed in a portable housing. In such embodiments, the unit may advantageously be physically associated with a monitored patient, such as, for example, attached in an arm band, a patient bed pouch, a hood or hat, a pocket of a shirt, gown, or other clothing, or the like. In other embodiments, the unit may be entirely or partially housed in a cable connector. In an embodiment, the signal processing and condition unit and/or the depth of consciousness monitor could also monitor patient parameters through other sensors including, for example, ECG, Sp02 from the earlobe, finger, forehead or other locations, blood pressure, respiration through acoustic or other monitoring technologies, or other clinically relevant physiological parameters.

In an embodiment, the depth of consciousness monitor communicates with a sensor, such as a forehead sensor including one or more light sources configured to emit light at a patient's forehead. In an embodiment, the light source may include one or more emitters or emitter systems, such emitters or emitter systems may be embedded into a substrate. In various embodiments, the emitters could include light emitting diodes ("LEDs"), lasers, superluminescent LEDs or some other light emitting components. These components could be arranged in any pattern on the substrate and could be either a single light emitting source or several light emitting sources. In an embodiment, the emitting components could emit light that deflects off of reflective surfaces associated with a cap of the substrate. The reflective cover could be any number of shapes or sizes and could be constructed to direct light to specific points or a point on the cap or substrate.

In an embodiment, a multi-faceted splitting mirror could reflect light to an opening in the substrate that would allow the light to escape and be emitted to an emission detector in an embodiment also housed in the light source substrate. The emission detector may advantageously sample the light providing feedback usable to create an optical bench or at least optical bench properties of the light source, including, for example, determinations of intensity, wavelength, or the like. In an embodiment, the light source may include a polarized filter for adjusting the emitter light, in some embodiments before exiting an opening in the emitter or being detected by the emission detector.

In an embodiment, a caregiver could analyze physiological information collected from the various sensors including a patient's temperature, EEG, brain oxygen saturation, stimulus response, electromyography or EMG, respiration using acoustic sensor applied to the through, body oxygen saturation, glucose concentration, or other blood analytes, pulse, hydration, blood pressure, perfusion, or other parameters or combinations of parameters to determine relevant information about the state of a patient's well-being. In another embodiment, a caregiver may advantageously analyze information collected from the various sensors to more completely assess the overall depth of a patient's sedation and obtain an assessment superior to an assessment derived from monitoring a single or a few of the parameters mentioned above.

Reference will now be made to the Figures to discuss embodiments of the present disclosure.

FIG. 1 illustrates one example of a depth of consciousness monitoring system 100. In certain embodiments, the depth of consciousness monitoring system 100 measures one or more physiological parameters including cerebral electrical activity (e.g., via EEG), cerebral muscular activity (e.g., via EMG), temperature, cerebral oxygenation, including venous and arterial oxygenation, arterial oxygenation at various other points on the body, various other blood analytes, including total hemoglobin, glucose, lipids, stimulus response, electromyography or EMG, respiration, pulse, hydration, blood pressure, perfusion, or other parameters or combination of other physiologically relevant patient characteristics. The information from these physiological parameters can be evaluated using trend analysis, absolute and relative measures of certain parameters, combined or alone to evaluate the total wellness and current state of sedation of a patient.

The depth of consciousness monitoring system 100 includes multiple or a single sensor 120 in communication with a depth of consciousness monitor 140 via a communications link 150. In the illustrated embodiment, the depth of consciousness monitoring system 100 also includes a drug delivery device 160 that receives a control signal from the depth of consciousness monitor 140 via a control link 170. The drug delivery device 160 provides one or more sedatives (e.g., narcotic, hypnotic, analgesic, opiate, etc.) to a patient 180 via a conduit 190.

The sensor 120 can include any variety of shapes and sizes, and could be applied to a variety of measurement sites on a patient's skin including any location on the forehead and temples or other location of the head. One example of a sensor 120 configured for placement on a patient's forehead is described below with respect to FIG. 3. The sensor 120 generally includes one or more electrodes and is configured to measure the electrical activity within the patient's head and generate an EEG signal, as discussed in further detail below.

In some embodiments, the sensor's electrodes are designed to be placed at a measurement site covered with a patient's hair. A caregiver or patient may fasten the sensor 120 to the patient's head with a variety of mechanism including adhesive, straps, caps, combinations of the same, or other devices for fastening sensors to a patient's body or skin known in the art.

In some embodiments, the communication link 150 and/or the control link 170 are wired electrical connections (e.g., an electrical cable, etc.). In other embodiments, the communication link 150 and/or the control link 170 utilize wireless communication to provide portability, and greater flexibility in depth of consciousness monitor placement with respect to the drug delivery device 160. Wireless communications also help accommodate an ambulatory patient, or other patient in transit. For example, in one embodiment, the depth of consciousness monitor 140 may be attached to an arm band or included in an arm band or other device that is wearable by the patient, including in a cap, a hood, a sling or a pocket of a garment. In such an embodiment, the sensor 120 communicates with the arm band depth of consciousness monitor 140 via a wired or a wireless connection.

In an embodiment, the depth of consciousness monitor 140 communicates wirelessly with the drug delivery device 160 over a wireless control link 170. This allows the depth of consciousness monitor 140 to be transported between various caregiving facilities, each with their own stationary drug delivery devices 160 without unhooking and reinserting hardwired electrical connections. Instead, the depth of consciousness monitor 140 could establish a wireless communication link with a stationary drug delivery device 160 as the depth of consciousness monitor 140 is brought into proximity with the drug delivery device 160. In an embodiment, the devices could establish the connection automatically and patient data may be automatically sent from the depth of consciousness monitor 140 to the drug delivery device 160. In other embodiments, caregiver interaction is required to establish a wireless control link 170 between the depth of consciousness monitor 140 and the drug delivery device 160. Such configurations advantageously facilitate portability and seamless monitoring of a patient while the patient is transported, for example, from an ambulance to a hospital room or from room to room within a hospital.

In an embodiment, the depth of consciousness monitor 140 also communicates with, or incorporates, a pulse oximeter (not shown). The pulse oximeter may be a multi-parameter monitor or other host device capable of monitoring a wide variety of vital signs and blood constituents and other parameters or combinations of parameters such as those monitors commercially available from Masimo Corporation of Irvine, CA, and disclosed herein with reference to U.S. Pat. Nos. 6,584,336, 6,661,161, 6,850,788, and 7,415,297, among others assigned to Masimo Corporation, and U.S. Patent Publication No. 2006/0211924, 2010/

0030040, among others assigned to Masimo Corporation or Masimo Laboratories, Inc. of Irvine CA, all of which are incorporated by reference in their entireties.

The communication link 150 and the control link 170 can include any of a variety of wired or wireless configurations. For example, in some embodiments the links 150, 170 are implemented according to one or more of an IEEE 801.11x standard (e.g., a/b/g/n, etc.), a BLUETOOTH wireless standard, and a wireless medical information communications standard, etc.

The drug delivery device 160 generally includes at least a drug therapy interface 192, a drug flow device 194, and a flow controller 196. The drug therapy interface 192 receives a drug and provides a flow path to the drug flow device 194. For example, the drug therapy interface 192 can include a port or receptacle to receive or interface with a drug capsule, intravenous bag, syringe, etc. The drug flow device 194 receives the drug therapy from the drug therapy interface 192 and allows the drug to flow to the patient 180 via the conduit 190. In some embodiments, the drug flow device 194 includes one or more of a solenoid, a pump, a valve, a peristaltic pump, a variable speed pump, a compression sleeve (e.g., to squeeze an intravenous bag), etc. The action and activation of the drug flow device 194 is controlled by the flow controller 196. The flow controller 196 includes a microcontroller, a memory, a signal input to receive a control signal from the depth of consciousness monitor 140 via the control link 170 and a signal output to provide control over the functionality of the drug flow device 194. The signal input can include a wireless radio to facilitate wireless communication over a wireless control link 170. The signal input allows closed-loop control over the operation of the drug delivery device 160, as will be described in greater detail below.

In some embodiments, the drug delivery device 160 is manually controlled by a clinician (e.g., an anesthesiologist) and/or includes a manual override to allow the clinician to take control over drug delivery to the patient 180. Therefore, in some embodiments, the depth of consciousness monitoring system 100 does not include an electronic control link 170 between the depth of consciousness monitor 140 and the drug delivery device. Instead, in such an open-loop configuration, the depth of consciousness monitor 140 displays an indication of the patient's depth of consciousness. The clinician is able to manually adjust drug therapy to the patient in response to the signals displayed by the depth of consciousness monitor 140.

In some embodiments, the depth of consciousness monitor 140 is configured to generate and/or provide a delay signal (which is a form of delay information) to the drug delivery device 160. The delay signal may be used by the drug delivery device to control whether the depth of consciousness monitoring system 100 is operating under positive or negative feedback. In some embodiments, the drug delivery device 160 controls or delays the delivery of drugs provided to the patient 180 in response to the delay signal. For example, the drug delivery device 160 may delay drug deliver to make sure that the depth of consciousness monitoring system 100 is operating under negative feedback, and is therefore a stable control system.

The delay signal can be determined by the depth of consciousness monitor 140 in any of a variety of manners. In one embodiment, the depth of consciousness monitor 140 time stamps the data received from the sensor 120 and provides the time stamp information or other related time information to the drug delivery device 160 as the delay signal. For example, in some embodiments, the delay signal includes the time stamp associated with the data received from the sensor 120 as well as a time stamp associated with the time the control signal data packet is sent to the drug delivery device 160. In other embodiments, the delay signal includes the difference between the two time stamps. In some embodiments, the drug delivery device 160 is configured to calculate or otherwise determine the appropriate control delay based upon the delay signal. For example, the drug delivery device 160 may time stamp the time the control signal is received from the depth of consciousness monitor 140. The drug delivery device 160 can determine a control delay based upon the difference between the time the control signal is received from the depth of consciousness monitor 140 and the time the depth of consciousness monitor received the signal from the sensor 120 that was used to generate the associated data packet received by the drug delivery device. The signal propagation delay through the depth of consciousness monitoring system 100 may be used to keep the system's feedback negative to avoid oscillation and to achieve stability.

In an embodiment, a caregiver or the patient may attach the depth of consciousness monitor 140 directly to the patient's arm or other part or clothing of the patient through an armband with straps or some other means known in the art to connect a portable monitoring unit to a patient. In an embodiment, a depth of consciousness monitor 140 may be integrated into a hat or other headgear wearable by the patient or some other structure near the patient. In an embodiment, the depth of consciousness monitor 140 can rest on a table or other surface near the patient.

In some embodiments, a depth of consciousness monitor 140 is integrated with the drug delivery device 160. Alternatively, the depth of consciousness monitor 140 could be a module that is docked or otherwise attached to the drug delivery device 160. The depth of consciousness monitor 140 can communicate with and/or be integrated with a variety of other device, such as a pulse oximeter, a respiration monitor, and EKG device, a blood pressure measurement device, a respirator, and/or a multi-parameter monitor.

Figure 2:
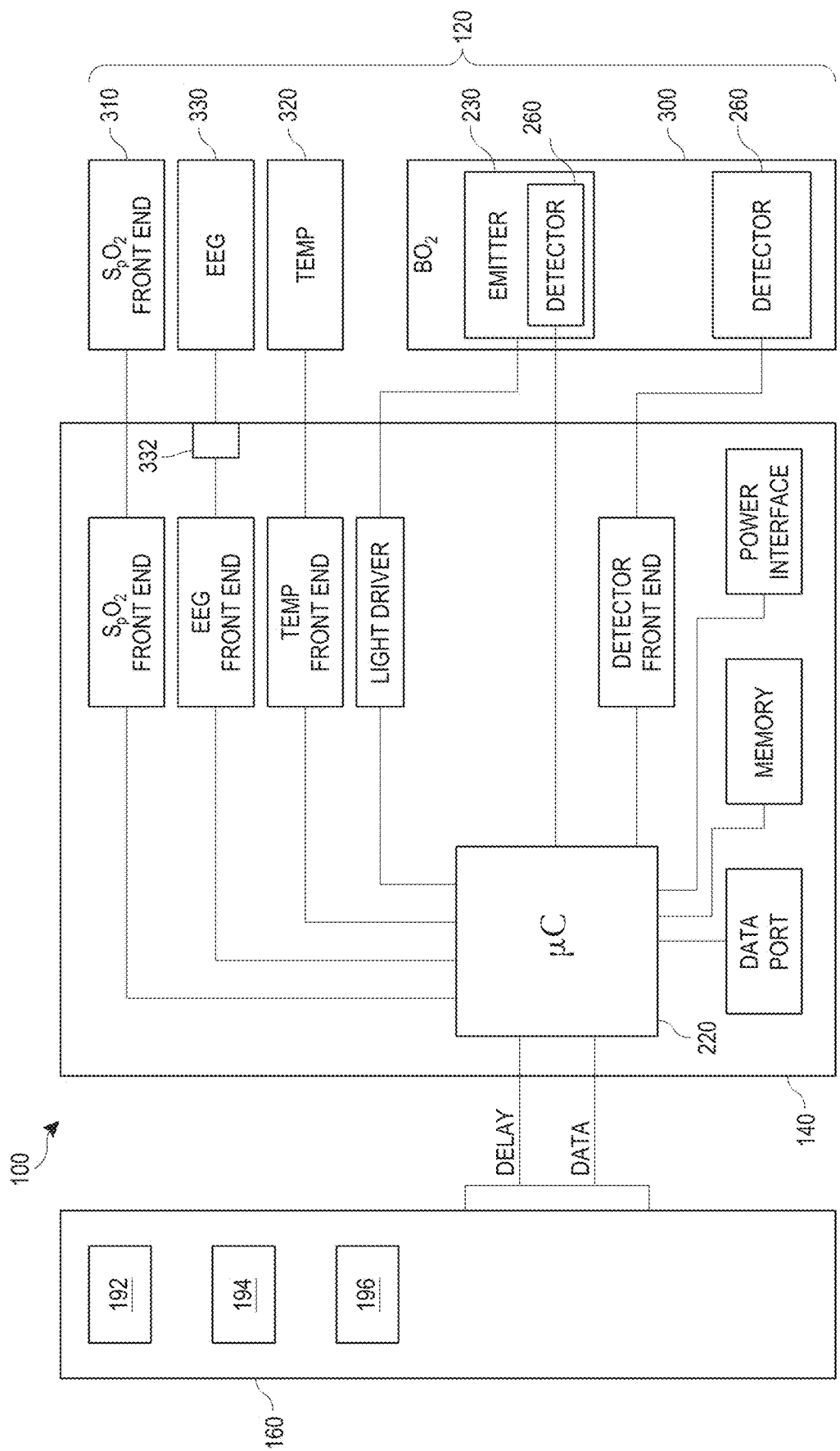
FIG. 2 illustrates a block diagram of one embodiment of the depth of consciousness monitor of FIG. 1.

FIG. 2 illustrates a block diagram of one embodiment of the depth of consciousness monitor 140, sensors 120, and drug delivery device 160. In an embodiment, the depth of consciousness monitor 140 includes a processor 220 which may be a micro-controller or other processor, to control and/or process signals received from the sensors 120. For example, the processor 220 may coordinate, process or condition, or manipulate the signals received from the sensor 120 to generate electronic data, control signals, and/or delay signals that are subsequently displayed and/or communicated to the drug delivery device 160. In addition, the processor 220 may receive instructions or data control messages from the drug delivery device 160 or other patient monitoring device to provide the appropriate conditioning and controlling of the various front end components of the sensors 120. Data transmitted between the depth of consciousness monitor 140, the drug delivery device 160, the sensors 120 and any other associated components, devices, or systems in communication with the depth of consciousness monitoring system 100 may be communicated by the devices using one or more interfaces, e.g., electrical wires, wireless communication, optical communication, RFID, LAN networks, or other electronic devices for communicating data known in the art. In one embodiment, a drug delivery device interface can include any one or more of electrical wires, wireless communication, optical communication, RFID, LAN networks, or other electronic devices for communicating data known in the art. In one embodiment, a multi-parameter physiological monitor interface can include any one or more of electrical wires, wireless communication, optical communication, RFID, LAN networks, or other electronic devices for communicating data known in the art.

The depth of consciousness monitor 140 may also include various front end components to enable the depth of consciousness monitor 140 to process the various signals received by the various sensors 120 that may be communicating with the depth of consciousness monitor 140. In an embodiment, front end components may translate and transmit instructions and control signals for driving the various sensors. In an embodiment, the front end components may translate, process, or transmit instructions and control signals to the emitting or light producing components of the sensor. The front end components may also receive and transmit data acquired by the detectors of the sensors to the microcontroller 220 or other processor 220. The front end components can include one or more of an analog-to-digital converter, a preamplifier, an amplifier, a filter, a decimation filter, a demodulator, etc.

These front end components could include front end components for a variety of sensors 120 including for sensors that detect blood oxygenation, EEG, EMG, ECG, temperature, acoustic respiration monitoring ("ARM") sensors, such as those available from Masimo Corporation of Irvine, CA, acoustic throat respiratory sensor, and brain oxygenation. In an embodiment, a caregiver could advantageously utilize a device with the ability to monitor the plurality of above mentioned parameters to more accurately determine a depth of a patient's sedation. However, in some embodiments, the depth of consciousness monitor 140 only includes EEG and EMG front end components. In an embodiment, a front end component that would be associated with a sensor 120 that detects brain oxygenation may have a sub component dedicated to driving emitters 230 associated with a light source of the brain oxygenation sensor and a sub-component associated with the detector 230 or detectors 230 of the brain oxygenation sensor 300 for receiving and transmitting the detected signals that pass through various body tissues. In other embodiments, the light drivers and detector front end are omitted.

In an embodiment, one of the various sensors associated with the front end components of the brain oximetry unit could be, for example, a blood oxygenation sensor 310 which may be placed at various measurement sites on a patient's skin, including the earlobe, finger, forehead or other places known in the art suitable for detecting blood oxygenation. Many suitable pulse oximeter sensors 310 are known in the art such as those blood oxygenation sensors 310 commercially available from Masimo Corporation of Irvine, CA, including but not limited to those described in U.S. Pat. Nos. 5,638,818, 6,285,896, 6,377,829, 6,580,086, 6,985,764, and 7,341,559, which are expressly incorporated by reference in their entireties.

In an embodiment, a temperature sensor 320 communicates with an associated front end component of the depth of consciousness monitor 140. The temperature sensor 320 detects the temperature of the skin, the temperature inside the ear, the temperature under the tongue, or any other temperature measurement method known in the art. In an embodiment, the temperature sensor 320 could be any suitable thermistor, or any other temperature sensor 320 known in the art capable of detecting a surface temperature of a patient's skin. Additional temperature sensor may advantageously provide feedback to the depth of consciousness monitor 140 regarding the performance or temperature of one, combinations of, or all of the emitters 230.

Figure 3:
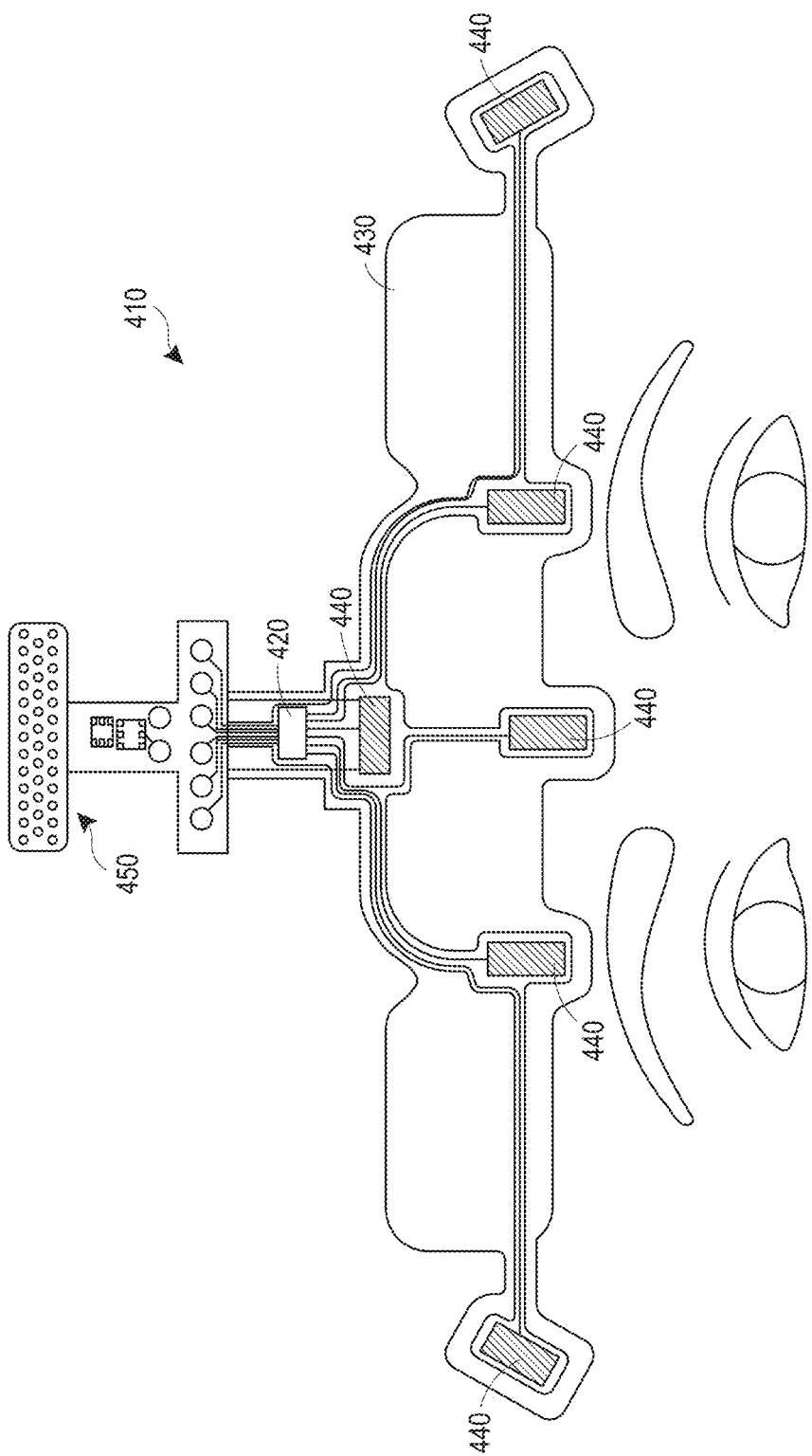
FIG. 3 illustrates one embodiment of the forehead sensor of FIG. 1.

An EEG sensor 330 may also be associated with the front end components of the depth of consciousness monitor 140. In an embodiment, the EEG sensor 330 may be any of a variety of EEG sensors 330 known in the art. An EEG sensor 330 could be applied to a patient at any of a multitude of locations and measurement sites on the skin of the head of a patient. In an embodiment, the EEG sensor 330 may include electrode leads that may be placed on a measurement site in contact with the skin of the patient. In an embodiment, the EEG 330 may monitor the electrical activity of a patient's brain through any number of electrodes, electrode leads, and channels or other systems known in the art. One such EEG sensor 330 is illustrated in FIG. 3 and described in greater detail below.

In an embodiment, the EEG sensor 330 may monitor and collect data from a patient's brain using 4 channels and 6 electrodes. In another embodiment, the EEG 330 may use 3 channels and 5 electrodes. In another embodiment, any variety or combination of sensors maybe be used that are suitable for obtaining an EEG signal, such as those described in U.S. Pat. Nos. 60/164,444, 6,654,626, 6,128,521, which are incorporated by reference in their entireties.

A brain oxygenation sensor 300 may also be associated with the front end components of the depth of consciousness monitor 140. In an embodiment, the brain oxygenation sensor 300 includes a light source 230, and a detector 260. The light source 230 of the brain oxygenation sensor 300 includes emitter(s) that would emit light, sonic or other radiation into the forehead at one, two or other plurality of measurement sites located on the skin of the patient at a plurality of predetermined wavelengths. In an embodiment, the brain oxygenation sensor 300 would include a detector 260 with photodiodes or other radiation detection devices to detect the radiation emitting from the patient at a one or two or a plurality of measurement sites on the skin of the head of a patient. Many suitable brain oxygenation sensors 300 and cerebral oximeters are known in the art including those disclosed in U.S. Pat. Nos. 7,072,701, 7,047,054, which are expressly incorporated by reference in their entireties.

In an embodiment, the light source 230 of the brain oxygenation sensor 300 may include an emission detector 260. In an embodiment, the emission detector 260 detects the light emitted from the light source 230 before passing through or contacting the measurement site of the patient. In an embodiment, an output from the emission detector 230 would be communicated to the micro-controller 220 of the depth of consciousness monitor 140 in order to calculate an approximate output intensity of the light emitted by the emitter(s) 230. The micro-controller 220 or other processor 220 could calculate the output intensity based on the output of the emission detector 260 by comparing the data to calibration data. In an embodiment, the calibration data could include measurement of intensity of light emitted from the emitter(s) 230 and corresponding measurements of output from the emission detector 260. This data could then be correlated to real time output from the emission detector 260 while the oxygenation sensor 230 is in use to determine an actual or approximate intensity of light or radiation being emitted by the emitter(s) 230 utilizing a calibration curve or other suitable calculation or processing method. In an embodiment, the calibration data may be stored in an EPROM or other memory module in the depth of consciousness monitor 140 or other patient processing module or device associated with the patient monitoring system 100.

In an embodiment, the detector 260 detects light or other radiation emitted from the light source 230 after, in an embodiment, some of the light has entered the measurement site on the patient and has been attenuated by a patient's tissue. In an embodiment, the detector 260 could be any number of detectors known in the art for detecting light or other radiation including photodiodes or other types of light or radiation detectors. In one embodiment, the detector 260 may convert detected light or other radiation into a signal, for example, an electrical output signal, which may represent the intensity or other attributes of the radiation. In an embodiment, the signal from the detector 260 may be sent to a brain oxygenation detector 260 front end located in the depth of consciousness monitor 140 for processing, conditioning or transmitting to a pulse oximeter (not shown) or other patient monitoring processor. In one embodiment, the signal may be converted into a digital format by an analog to digital converted located in the depth of consciousness monitor 140. In an embodiment, the data from the detector 260 of the brain oxygenation sensor 300 may be processed to determine the cerebral oxygenation of a patient's brain tissue. In an embodiment, the processing of the data may include determining the changes of intensity between various wavelengths of emitted and detected light of the cerebral oxygenation sensor 300.

In an embodiment, a cerebral oximeter or multi-parameter monitor (not shown) acquires data from the depth of consciousness monitor 140 or sensor 120 derived from physiologically relevant parameters. In an embodiment, the pulse oximeter could provide visual quantitative or qualitative assessments of the patient's well-being based on one or more of the various parameters or physiological attributes measured.

In an embodiment, a caregiver may utilize various physiological parameters to make a quantitative assessment of the patient's depth of sedation as indicated by an index based on for example, a patient's temperature, electroencephalogram or EEG, brain oxygen saturation, stimulus response, electromyography or EMG, respiration based on acoustic through sensors, body oxygen saturation or other blood analytes, pulse, hydration, blood pressure, perfusion, or other parameters or combinations of parameters. In another embodiment, various aspects of sedation could be assessed quantitatively or qualitatively based on a visual representation of the patient's sedation in the aspects including hypnosis, responsiveness, muscle relaxation or other clinically relevant facets of depth of anesthesia.

In an embodiment, the functionality of the depth of consciousness monitor 140 could be optionally controlled by the drug delivery device 160. In an embodiment, the data and qualitative and quantitative assessments of a patient's wellness being could be displayed on one or more of the depth of consciousness monitor 140, the drug delivery device 160, or any other device or system in communication with the depth of consciousness monitoring system 100 (e.g., a pulse oximeter, physiological patient monitor, nurse station, etc.). Also, audible alarms and other indicators could be displayed on either or both the depth of consciousness monitor 140 and drug delivery device in response to various threshold breaches based on the assessment of the patient's wellness and depth of consciousness as determined from the various monitored parameters.

FIG. 3 illustrates one embodiments of a sensor 120 in the form of an EEG sensor 410, which is configured for placement on a patient's forehead to generate an EEG signal. Disposable and reusable portions of the sensor 410 may be connected and overlayed on top of one another. The EEG sensor 410 includes six EEG electrodes 440 with two reference electrodes (along the central axis of the EEG sensor 410) and four active channel electrodes (two on each side of the EEG sensor's central axis). In some embodiments, light source(s) and light detector(s) (not shown) may be incorporated into the EEG sensor 410, as well. All or some of the above mentioned sensor components including the EEG electrodes 440, leads from the electrodes 440, and blood oxygen detecting light emitters and detectors (when provided) may communicate with one or more chips 420 that enables transmission of acquired signals and drive signals. In some embodiments a single chip 420 is provided. In other embodiments, each component communicates with its own individual chip through wires, or printed circuits, or other suitable electrical connections.

The EEG electrodes 440 may be any suitable electrodes for detecting the electro-potentials on the surface of the skin of a patient's head. In one embodiment, EEG electrodes 440 include a metal or other suitable conductor and utilize leads contacting the surface of the skin. In another embodiment, the electrodes 440 are gelled electrodes that make contact through the skin via gel and have metal leads that come into contact with the gel. In still yet another embodiment, the EEG electrodes 440 may be glued to the forehead with any suitable patient dermal adhesive for connecting the EEG electrodes 440 and may have electrical conductivity. In an embodiment, potentials from the EEG electrodes 440 are transmitted to the depth of consciousness monitor 140 for further conditioning, transmitting or processing.

The sensor 410 may also include one or more temperature sensors (not shown). The temperature sensor may be any suitable sensor that can detect the temperature of the surface of the skin or other patient temperatures. In an embodiment, the temperature sensor may include a thermistor attached to a reusable portion of the sensor 410.

In an embodiment, the sensor 410 includes an interface 450 to couple the sensor 410 to the depth of consciousness monitor 140. The interface 450 may be any suitable electrical or data connection or communication port or device including, for example, a pin connector and receiver. Various other communication or electrical connections known in the art may be utilized. In an embodiment, the interface 450 may include an inductance connection utilizing transformers to couple a data and electrical connection across an insulator. In another embodiment, the interface 450 provides a data or electronic coupling between a reusable portion and a disposable portion of the sensor 410.

In some embodiments, the sensor 410 includes a disposable portion (not shown) removably attached to a reusable portion (not shown). In an embodiment, the disposable portion attaches to a measurement site of a patient's head and provides a base to which the reusable portion may be docked, mated or connected. The disposable portion houses the components of the sensor 410 that may be less expensive than at least some of the components contained in the reusable portion, and therefore may be disposed after a single or multiple uses, either on the same patient or different patients. The disposable portion of the sensor 410 includes a tape substrate that provides a base or substrate to which at least some of the components of the disposable portion may adhere or be integrated. In an embodiment, the tape can be constructed from any suitable disposable material that will effectively hold the components includes in the disposable portion to a patient's forehead or other measurement site. In an embodiment, the tape includes a suitable dermal adhesive on a patient side of the disposable portion for temporary adhesion of the sensor to a patient's skin.

In an embodiment, the sensor 410 may include an adhesive tape 430 that supports the EEG electrodes 440. In one embodiment, the EEG electrodes 440 may be fastened to the tape 430. In an embodiment, the EEG electrodes 440 could be embedded in the tape 430 by any known adhesive in the sensor arts or any other suitable means for connecting the EEG electrodes 440 that would allow the EEG electrode 440 leads to be exposed on a patient side of tape 430 in an appropriate position to come in close proximity to a measurement site of a patient's skin. In an embodiment, EEG electrodes 440 may be gelled so that the gel contacts the electrodes and a measurement site of a patient's skin to provide an electrical path between the measurement site of the patient's skin and the EEG electrodes 440. In an embodiment, the leads of the EEG electrodes 440 are connected to a chip 420 by wires or other suitable electrical connections, such a as a printed circuit, flex circuit, etc.

The sensor 410 may also include a temperature sensor (not shown). In an embodiment, the temperature sensor includes a thermistor with the thermistor leads exposed on a patient contacting side of the tape 430, in order to facilitate the contacting of the leads of temperature sensor to a measurement site of a patient's skin. In an embodiment, the temperature sensor is connected to single chip through wires or other suitable electrical connections such as a flexible printed circuit. In an embodiment, the temperature sensor may be located anywhere on the tape 430, the disposable portion or the reusable portion of the sensor 410 (if the sensor is provided with disposable and reusable portions). In an embodiment, the leads for the temperature sensor may be near the center of tape 430 or anywhere on the periphery of tape 430.

In some embodiments, the sensor 410 includes a pulse oximeter sensor (not shown). The pulse oximeter sensor can include an ear pulse oximeter sensor that emits and detects radiation to determine the oxygenation of the blood travelling through the arteries of the ear. Many suitable ear pulse oximeter sensors are known in the art such as those sensors commercially available from Masimo Corporation and disclosed herein with reference to U.S. Pat. No. 7,341,599, which is expressly incorporated by reference in its entirety. In another embodiment, the pulse oximeter sensor may be a forehead pulse oximeter sensor or any other suitable pulse oximeter known in the art or disclosed herein. The pulse oximeter sensor may be connected to the sensor 410 through electrical wires, wirelessly or other suitable electrical or data connection. Data collected from the pulse oximeter sensor may be transmitted to the depth of consciousness monitor 140, pulse oximeter, or both for conditioning and further processing.

In some embodiments, signal processing and conditioning circuitry of depth of consciousness monitor configured to monitor the EEG signals of a patient and providing feedback on the depth of sedation or awareness of a patient undergoing anesthesia, may be partially or entirely incorporated into the sensor 410. Sedation brain function monitors, including those similar to the SEDLINE sedation monitor commercially available from Masimo Corporation of Irvine, CA, as well as those described in U.S. Pat. Nos. 6,128,521, 6,301,493, 6,317,627, 6,430,437, all of which are expressly incorporated by reference in their entireties. For example, the sensor's connector or interface 450 may house the circuit board, with six channels for six detectors and a processor configured to determine depth of consciousness.

Integration of all or the majority of the associated circuitry and processing components of several different patient monitoring sensors in a single sensor advantageously provides a caregiver a simple device that can be attached to the patient's forehead and/or other areas on the patient, to provide minimal discomfort to the patient and minimal amount of wires and connections to cause electrical interference with instruments in the hospital environment. Additionally, the caregiver will spend less time attaching various sensors to a patient where each would otherwise require its own associated monitoring station. Furthermore, integration of sensor processing components allows some of the processing components to have shared functionality and therefore saves considerably on manufacturing costs. For example, memory chips, processors, or other electrical components may be shared by the various sensors.

EEG Signal Processing

Referring again to FIG. 2, the depth of consciousness monitor's processor 220 is configured to receive at least an EEG signal from an EEG sensor 330 using an interface, such as an EEG interface 332 and process the EEG signal to determine the patient's depth of consciousness. In some embodiments, the processor 220 determines an index value between 0 and 100 to indicate depth of consciousness. The depth of consciousness monitor 140 may include a display, such as a monitor, LED, speaker, etc., to indicate the patient's depth of consciousness, e.g., the index value.

Figure 4:
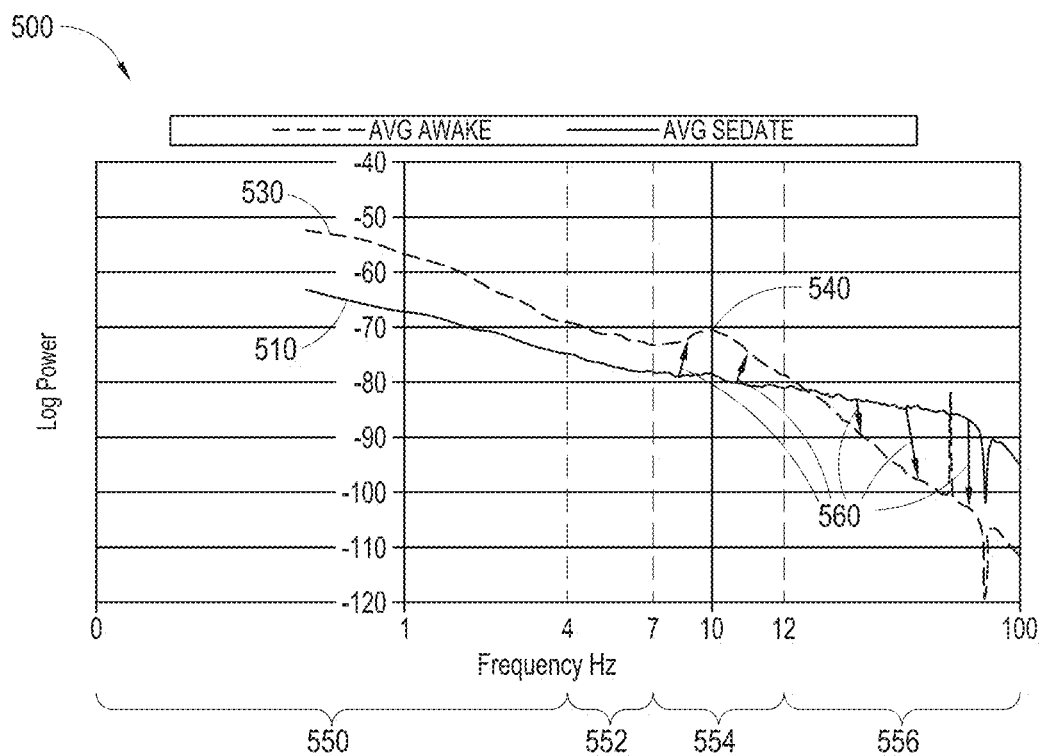
FIG. 4 illustrates one embodiment of an EEG frequency spectrum of the patient before and during sedation using the depth of consciousness monitor of FIG. 2.

In some embodiments, the processor 220 determines the frequency content of the EEG signal prior to administration of any sedatives as well as during sedation. FIG. 4 illustrates one embodiment of a graph 500 showing the patient's EEG's frequency content or frequency spectrum prior to sedation as curve 510 and during sedation as curve 530. Shifting of the curve 510 amplitude at frequencies below 10 Hz, a drop in curve slope at frequencies above 10 Hz, and the formation or increase in the frequency curve 510 to form a local maximum (e.g., local maximum 540) at 10 Hz each indicates that the patient has entered a sedated state.

Indeed, in one embodiment, the processor 220 determines whether the patient is adequately sedated by monitoring for the presence of a local maximum 540 in the frequency curve 530 above a predetermined threshold value, at 10 Hz. However, the shape of the frequency curve 530 can vary based upon several factors, such as any one or more of the patient's age, age classification (e.g., pediatric, adult, geriatric, etc.), sex, weight, body-mass index, genetic factors, etc. The shape of the frequency curve 530 can also vary based upon one or more physiological parameters associated with the patient, such as the patient's temperature, blood oxygen concentration, EMG signal, etc. Furthermore, the shape of the frequency curve 530 can also vary based upon the particular drug administered to sedate the patient. For example, the drug type, drug class (e.g., hypnotic, analgesic, opiate, etc.), mechanism or method of delivery (inhalant, intravenous, ingestible, etc.) and/or particular active ingredient (e.g., Propofol (TIVA), Sevoflurane, nitrous oxide, morphine, etc.) can each affect the shape of the frequency curve 530. Variations in the frequency curve 530 make it more difficult for the depth of consciousness monitor 140 to accurately determine whether the patient is adequately sedated.

Therefore, to improve accuracy, in one embodiment the depth of consciousness monitor's processor 220 analyzes the frequency curve 530 by considering one or more curve profiles associated with the patient and/or the drug administered. For example, in one embodiment, the processor 220 obtains physiological information regarding the patient from sensors 120 attached to the depth of consciousness monitor 140. In other embodiments, the processor 220 obtains physiological information regarding the patient via a data port.

For example, the data port can receive temperature, blood oxygen saturation, respiration rate, and/or other physiological parameter information from an separate monitor. In addition, the depth of consciousness monitor 140 can receive additional information regarding the patient and the drug via the data port, as well.

For example, in some embodiments, the data port includes a wireless radio, a network adapter, a cable, an Ethernet adapter, a modem, a cellular telephone, etc., to receive patient and/or drug information. The patient and/or drug information is provided to the processor 220 to accurately interpret the frequency curve 530 derived from the EEG sensor 330 signal. In one embodiment, the data port includes a keyboard or other data entry device that allows the clinician to manually inter data relating a patient or drug parameters, such as those examples described above. Indeed, the processor 220 can include one or more EEG processing engines that are configured based upon the patient and/or drug data received by the depth of consciousness monitor 140, as discussed in greater detail below.

In some embodiments, the patient's frequency response graph 500 is processed as four distinct, non-overlapping frequency bands 550, 552, 554, 556. For example, the first frequency band, sometimes referred to as the delta band, is the portion of the graph 500 between 0 and 4 or about 4 Hz. The second frequency band, sometimes referred to as the theta band, is the portion of the graph 500 between 4 or about 4 Hz and 7 or about 7 Hz. The third frequency band, sometimes referred to as the alpha band, is the portion of the graph 500 between 7 or about 7 Hz and 12 or about 12 Hz; and the fourth frequency band, sometimes referred to as the beta band, is the portion of the graph 500 greater than 12 or about 12 Hz.

In some embodiments, the depth of consciousness monitor 140 determines whether there is a peak 540 greater than a predetermined threshold in the frequency curve 530 anywhere within the alpha band 554. If so, the monitor 140 may determine that the patient is adequately sedated. However, in some cases, the peak 540 can shift and appear outside of the alpha band 554. For example, a sedated patient that is experiencing hypothermia may not manifest a peak in the alpha band; instead, the peak may shift to the theta or beta bands.

Therefore, in one embodiment, the depth of consciousness monitor 140 does not limit its search for a peak 540 to a particular frequency value (e.g., 10 Hz) or a particular frequency band (e.g., alpha band 554). Instead, in such an embodiment, the depth of consciousness monitor 140 scans across all frequencies (or a larger subset of frequencies than just those within the alpha band) to search for a peak 540 (e.g., across two or more frequency bands). A detected peak may be used to determine alone (or in combination with other patient and/or drug data) whether the patient is adequately sedated.

The peak 540 can be defined in any of a variety of clinically-relevant manners. For example, the peak 540 can be defined based upon the slope of the curve segment on one or both sides of the peak 540, the relative magnitude of the peak compared to the curve values at predetermined locations or offsets on either side of the peak 540, the relative magnitude of the peak compared to the frequency curve 510 of the patient obtained prior to sedation, etc.

In one embodiment, the processor 220 processes the patient's frequency spectra curve 510, 530 as deformable curves by utilizing motion vector processing. For example, the processor 220 compares each point (or a predetermined number of points) in the pre-sedation curve 510 to points within the sedation frequency curve 530 to match points having the greatest similarity (e.g., relative position with respect to its neighbors, pattern matching, sum of absolute differences, any pattern matching technique, etc.). The processor 220 determines one or more motion vectors 560 to describe the motion of the points from one curve 510 to the next 530. Each motion vector 560 includes both direction and amplitude (e.g., distance traveled) information. Although the graph 500 includes curve 510, 530 illustrated in the frequency domain (the x-axis represents frequency), the motion vectors 560 include time domain information. For example, the processor 220 can look at multiple frames of data (e.g., multiple graphs 500) and employ pattern matching techniques (e.g., sum of absolute differences) to determine which points in the graphs 500 and their curves 510, 530 to use to define the respective motion vectors 560. In some embodiments, the motion vectors 560 are determined at 0.5, 1, 2, or 2.5 Hz intervals.

One or more motion vector 560 profiles may be constructed based upon particular drug and patient data. For example, each drug used for sedation may be characterized by a unique set of motion vectors. When a patient is treated with a particular drug, and the patient's motion vectors match those of the drug (e.g., the drug profile), the processor 220 can determine that the patient is adequately sedated. Such profiles may be determined for any one or more of the patient's age, age classification (e.g., pediatric, adult, geriatric, etc.), sex, weight, body-mass index, genetic factors, etc., physiological parameters associated with the patient, such as the patient's temperature, blood oxygen concentration, EMG signal, etc., the particular drug administered to sedate the patient, the drug type, drug class (e.g., hypnotic, analgesic, opiate, etc.), mechanism or method of delivery (inhalant, intravenous, ingestible, etc.) and/or particular active ingredient (e.g., Propofol (TIVA), Sevoflurane, nitrous oxide, morphine, etc.). Such profiles may be stored within the depth of consciousness monitor's memory, or they may be retrieved from one or more data repositories stored at one or more remote locations (e.g., over a computer network, over the Internet, from a server, from the cloud, etc.).

In another embodiment, the EEG front end circuitry is configured not to eliminate or filter out low frequencies. The EEG front end circuitry instead allows the processor 220 to determine slow waves (e.g., time-domain signals at or below 1, 0.5, and/or 0.2 Hz). The processor 220 can employ one or more phase coherence methods to detect phase coherence between one or more slow waves and one or more patient signals falling within one of the frequency bands 550, 552, 554, 556. For example, in some embodiments, phase coherence between a slow wave and a signal from the theta band 552 indicates that the patient is awake. Once the slow wave and signal from the theta band 552 are out of phase, the patient is sedated. In other embodiments, phase coherence analysis is performed to compare phase coherence between a selected slow wave and a different frequency band's signals (e.g., the delta band 550, the alpha band 554, and/or the beta band 556). In some embodiments, the processor 220 performs phase coherence analysis between a selected slow wave and multiple signals between 4 and 50 Hz, e.g., every 0.2, 0.5, 1, or 2 Hz. In other embodiments, phase coherence is determined along the entire frequency spectrum.

In yet another embodiment, the processor 220 generates and/or utilizes a mathematical or electrical model of brain activity to determine whether the patient is adequately sedated. The model can be used to predict what the EEG of a sedated patient should look like based upon a particular drug, drug delivery mechanism, concentration (or any other drug parameter, including those discussed above). Actual EEG signals may be compared to the signal predicted by the model to determine whether the patient is adequately sedated. The model can be constructed of various combinations of electrical components (e.g., resistors, capacitors, amplifiers, etc.) or computing elements.

In one embodiment, brain modeling occurs by storing EEG signals from sedated patients in a memory location and categorized the EEG signals based upon any of a variety of drug and patient data information. For example, sedated EEG signals may be categorized based upon the particular drug, dosage, concentration, delivery method, etc. used to treat the patient. A brain response model is constructed by combing the various data into a single model.

Figure 5:
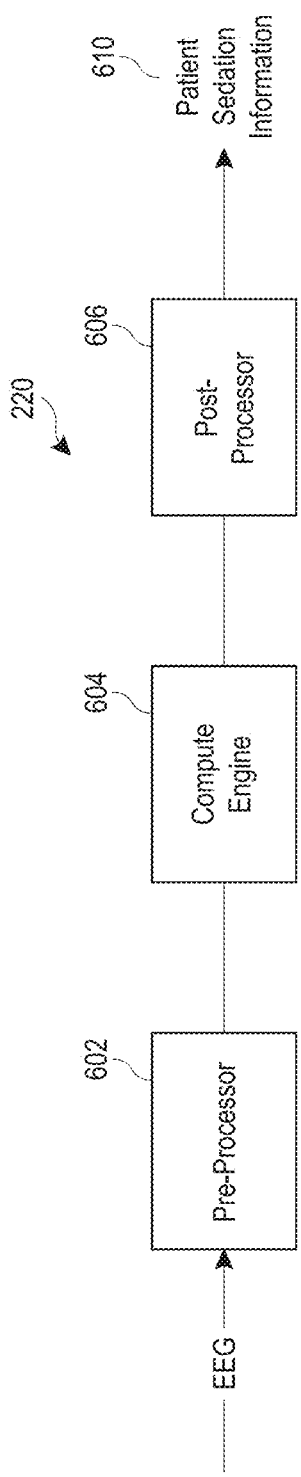
FIG. 5 illustrates one embodiment of the processor of the depth of consciousness monitor of FIG. 2.

In some embodiments, the processor 220 includes a pre-processor 602, a compute engine 604, and a post processor 606, as illustrated in FIG. 5. The patient's EEG signal is received by the pre-processor 602. The pre-processor 602 performs front end processing, such as one or more of filtering, amplification, A/D sampling, decimation, demodulation, etc. of the EEG signal. In some embodiments, the pre-processor 602 includes the EEG front end functionality discussed above with respect to FIG. 2. The compute engine 604 determines the level of patient sedation and/or depth of consciousness utilizing, for example, any of the techniques described herein. In one embodiment, the compute engine 604 determines an index value representative of the patient's sedation level. The post-processor 606 provides an indication of the patient's sedation level as well as other relevant information (e.g., system delay, as discussed above, other physiological parameter information, pass-through signals, etc.) for display to the clinician and/or transmission to a drug delivery device or other physiological monitor or information display station. In some embodiments, the post-processor 606 stores patient sedation, EEG signals, patient data and drug information in a memory location.

Figure 6:
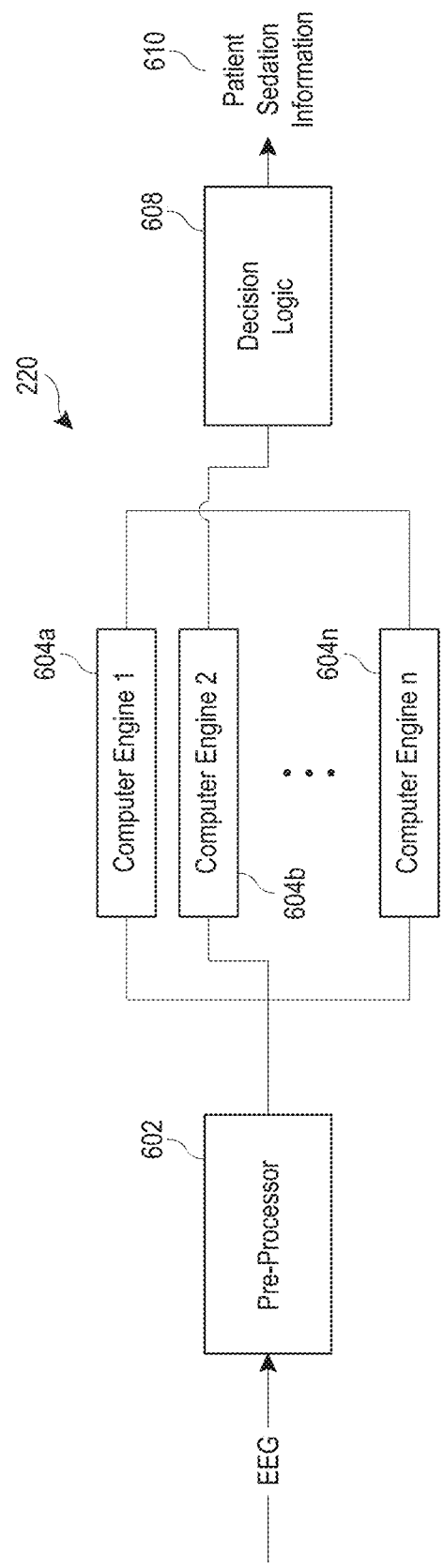
FIG. 6 illustrates another embodiment of the processor of the depth of consciousness monitor of FIG. 2.

Another embodiment of a processor 220 is illustrated in FIG. 6. The processor 220 includes a pre-processor 602, multiple compute engines 604a, 604b, . . . 604n, and decision logic 608. Each compute engine 604a, 604b, . . . 604n determines patient sedation information utilizing different processing approaches. For example, one compute engine 604 may determine patient sedation information utilizing motion vector analysis (e.g., as discussed above), one compute engine 604 may determine patient sedation information utilizing frequency coherence analysis (e.g., as discussed above), etc. Furthermore, each compute engine 604 can be drug or patient information specific. For example, the compute engine 604 may utilize historical information (either of the patient himself or from a model, etc.) to determine patient sedation. Each compute engine 604 could therefore correspond to a particular patient's age, age classification (e.g., pediatric, adult, geriatric, etc.), sex, weight, body-mass index, genetic factors, etc., physiological parameters, such as temperature, blood oxygen concentration, EMG signal, etc., the particular drug administered to sedate the patient, such as the drug type, drug class (e.g., hypnotic, analgesic, opiate, etc.), mechanism or method of delivery (inhalant, intravenous, ingestible, etc.) and/or particular active ingredient (e.g., Propofol (TIVA), Sevoflurane, nitrous oxide, morphine, etc.). The compute engines 604 may operate simultaneously to parallel process EEG information.

A decision logic module 608 receives the outputs of each compute engine 604 and applies logic to determine the best estimate of the patient's sedation level. For example, in some embodiments, the decision logic module 608 averages or weighted averages the outputs of the compute engines 604. In other embodiments, the decision logic module 608 selects one or more compute engine outputs based upon known information about the patient and/or drug(s) used for sedation. The decision logic output 610 can indicate one or more parameters relevant to patient sedation. For example, in some embodiments, the decision logic output 610 includes suppression bar, EMG estimation, patient sedation index, drug type and patient age estimates. If any one or more decision logic outputs do not match actual drug or patient profile information, an alarm can activate. In other embodiments, the clinician manually compares the decision logic outputs to actual drug and patient profile information to confirm the accuracy of the depth of consciousness monitor 140.

Figure 7:
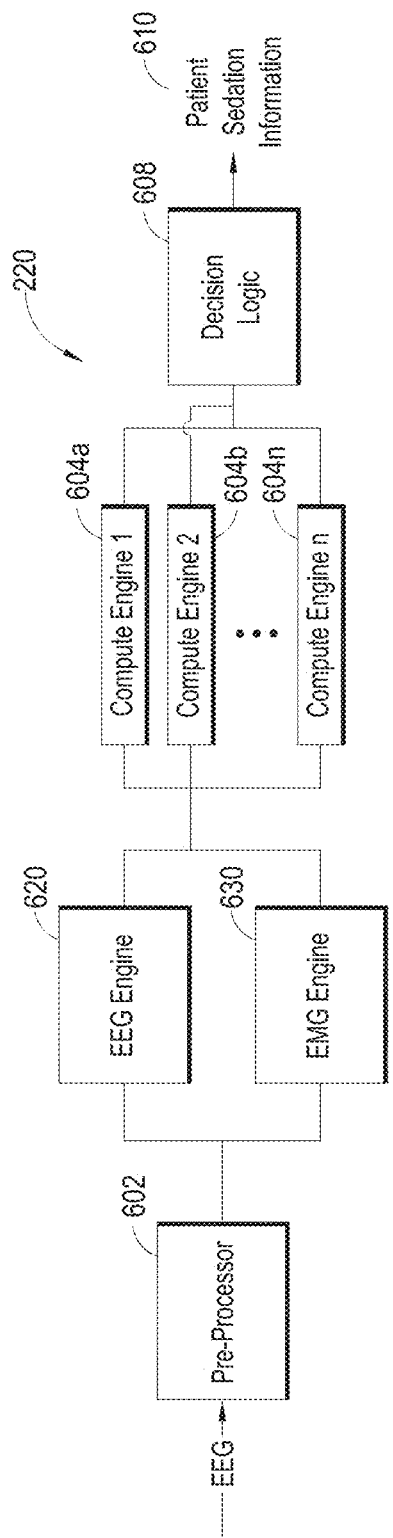
FIG. 7 illustrates yet another embodiment of the processor of the depth of consciousness monitor of FIG. 2.

Another embodiment of a depth of consciousness monitor's processor 220 is illustrated in FIG. 7. The processor 602 includes a pre-processor 602, compute engines 604 and decision logic 608, as discussed above with respect to FIG. 6. In addition, the processor 220 includes an EEG engine 620 and an EMG engine 630. The EEG and EMG engines receive a pre-processed EEG signal from the pre-processor 602. The pre-processed EEG signal will generally contain both EEG and EMG content. For example, EEG content describes the electrical activity within the patient's brain and the EMG content describes the electrical activity associated with the muscular contractions in the patient's forehead, near the EEG sensor. The EEG and EMG engines 620, 630 separate the EEG and EMG content from the pre-processed EEG signal. The outputs of the EEG and EMG engines 620, 630 communicate with the inputs of one or more compute engines 604. The EEG signal from the EEG engine provides an indication of the patient's hypnotic state, while the EMG engine provides an indication of the patient's analgesic response, or pain state. Separating the two provides more information about the patient's state, and allows improved depth of consciousness processing. When EMG content is included in the EEG signal, the frequency response curve is flatter at higher frequencies (e.g., at frequencies in the beta band).

Figure 8:
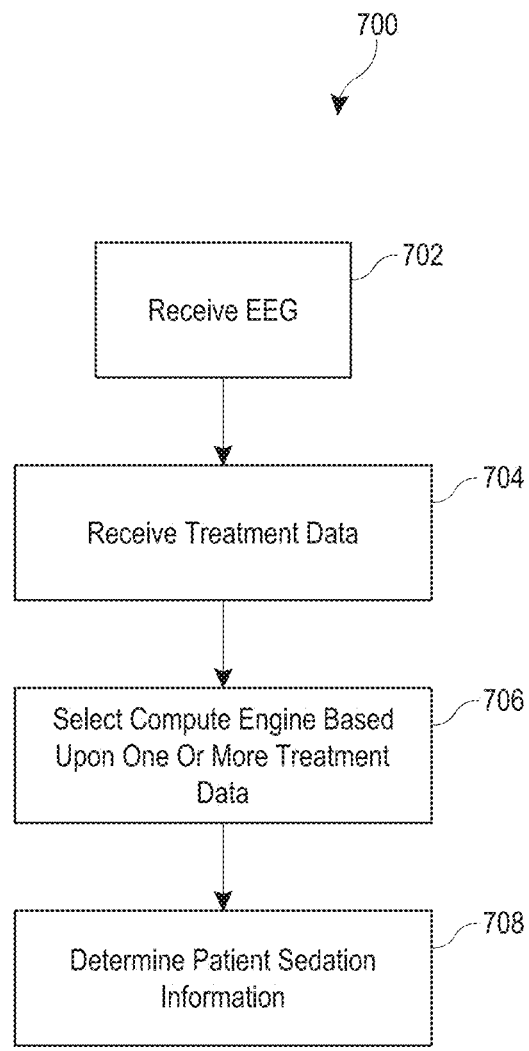
FIG. 8 illustrates one embodiment of a routine to determine patient sedation information that can be performed by any of the processors of FIGS. 5-7.

FIG. 8 illustrates one embodiment of a process 700 to determine a patient's sedation level that can be implemented by any of the processors described above. The process 700 begins at block 702. At block 702, the process 700 receives an EEG signal from a patient. At block 704, the process 700 receives treatment data. The treatment data may include one or more of patient data and drug profile information. The patient data can include any of the patient data or drug profile information described above. At block 706, the process 700 selects a computing engine based upon one or more treatment data. At block 708, the process 700 computes patient sedation information using EEG information and the selected computing engine. The patient sedation information can include one or more of a patient sedation level or index, an EMG level, a prediction of the drug used to sedate the patient, a prediction of the patient's age, etc. The process 700 ends at block 708.

Figure 9:
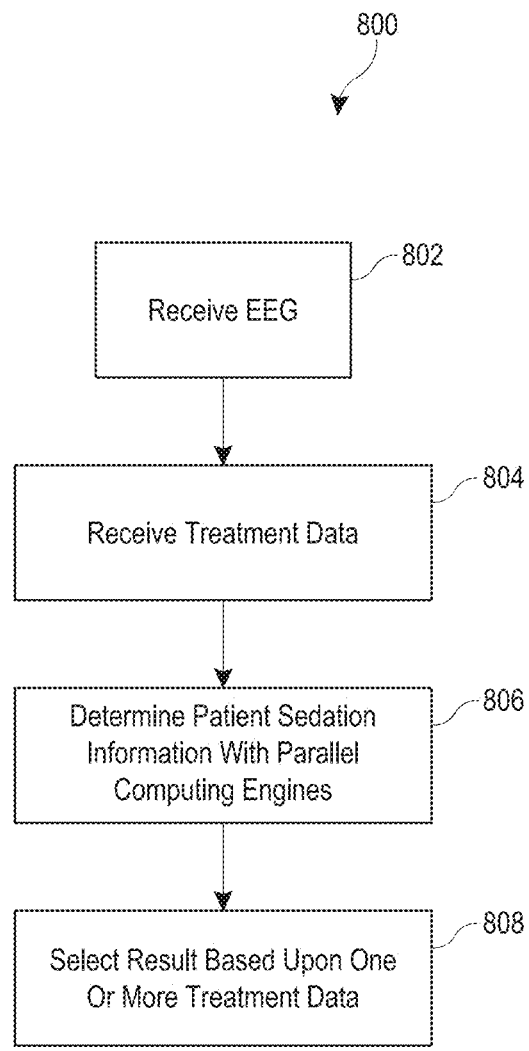
FIG. 9 illustrates another embodiment of a routine to determine patient sedation information that can be performed by any of the processors of FIGS. 5-7.

FIG. 9 illustrates another embodiment of a process 800 to determine a patient's sedation level that can be implemented by any of the processors described above. The process 800 begins at block 802. At block 802, the process 800 receives an EEG signal from a patient. At block 804, the process 800 receives treatment data. The treatment data may include one or more of patient data and drug profile information. The patient data can include any of the patient data or drug profile information described above. At block 806, the process 800 computes patient sedation information with parallel computing engines using the EEG information. The patient sedation information can include one or more of a patient sedation level or index, an EMG level, a prediction of the drug used to sedate the patient, a prediction of the patient's age, etc. At block 808, the process 800 determines patient sedation information by selecting the output of one of the parallel computing engines, or by combining one or more computing engine outputs (e.g., averaging, weighted averaging, etc.). The process 800 ends at block 808.

Figure 10:
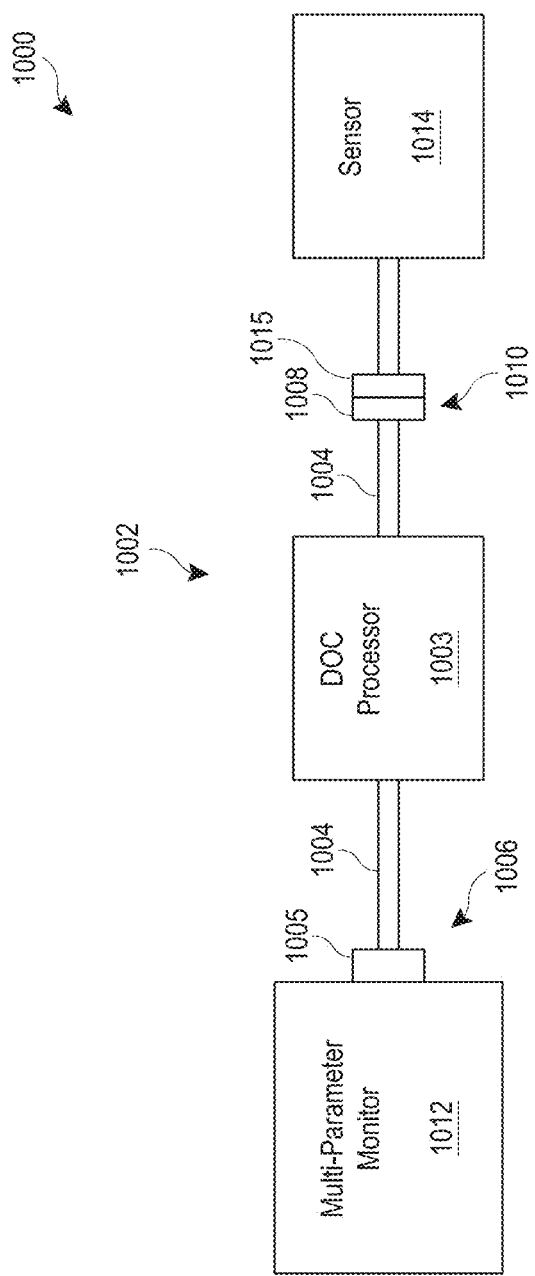
FIG. 10 illustrates another embodiment of a depth of consciousness monitoring system.

FIG. 10 illustrates one embodiment of a depth of consciousness monitoring system 1000. The system 1000 includes a depth of consciousness monitor assembly 1002, a multi-parameter monitor 1012, and a sensor 1014. The monitor assembly 1002 includes a depth of consciousness processor 1003, which can include any of the processors described above. In some embodiments, the processor 1003 is configured to perform one or more of the methods described above.

The assembly 1002 may be provided in the form of a cable. For example, the assembly 1002 may include one or more cables 1004 (or cable portions) that terminate in connectors 1005, 1008 located at the cable ends 1006, 1010. In the illustrated embodiment of FIG. 10, the assembly 1002 includes two cables 1004. The first cable 1004 has two ends and is coupled to the processor 1003 at one end and terminates at a connector 1005 at the other end 1006. In one embodiment, the connector 1005 (which is one embodiment of an interface, such as a multi-parameter monitor interface) is configured facilitate communication between the processor 1003 and a medical device, such as a physiological monitor, display instrument, and/or a multi-parameter monitor 1012, etc. In some embodiments, the connector 1005 receives power from a multi-parameter monitor 1012 to power the depth of consciousness processor 1003. In some embodiments, the processor 1003 is configured to consume less than about 250 mW, 500 mW or 1 W at about 4.75 V, 5 V or 5.25 V.

Physiological signals generated by the depth of consciousness processor 1003 are communicated to the multi-parameter monitor 1012 via the connector 1005. The multi-parameter monitor 1012 is configured to display one or more of the signals generated by the depth of consciousness processor 1003. In one embodiment, the cable 1004 that terminates at the multi-parameter monitor 1012 connector 1005 is configured to provide and/or receive power, ground, data+ and data− signals. For example, in one embodiment, the cable 1004 includes four conductors, one each for power, ground, data+ and data−.

An adapter or coupler (not shown) may be provided to facilitate coupling of the connector 1005 to the multi-parameter monitor 1012. For example, an adapter having first and second ends can be configured to have different shapes and pin configurations to allow communication and physical coupling of the connector 1005 to the multi-parameter monitor 1012. In some embodiment, the adapter (not shown) also includes conditioning circuitry to facilitate communication and/or power transmission between the multi-parameter monitor 1012 and the processor 1003. For example, the adapter may provide voltage regulation, electrical isolation, signal multiplexing, etc.

The second cable 1004 has two ends and is coupled to the processor 1003 at one end and terminates at a connector 1008 at the other end 1010. In one embodiment, the connector 1008 is configured to facilitate communication with a physiological sensor 1014, such as an EEG sensor, and/or any other sensor described above via an interface 1015 (e.g., interface 450 of FIG. 3). In one embodiment, power from the multi-parameter monitor 1012 is directly or indirectly (e.g., after further filtering, conditioning, pulsing, etc. by the processor 1003) communicated to the sensor 1014. Signals (e.g., e.g., measured patient signals) from the sensor 1014 are communicated to the processor 1003 via the interface 1015, which can be coupled to the connector 1008.

Figure 11:
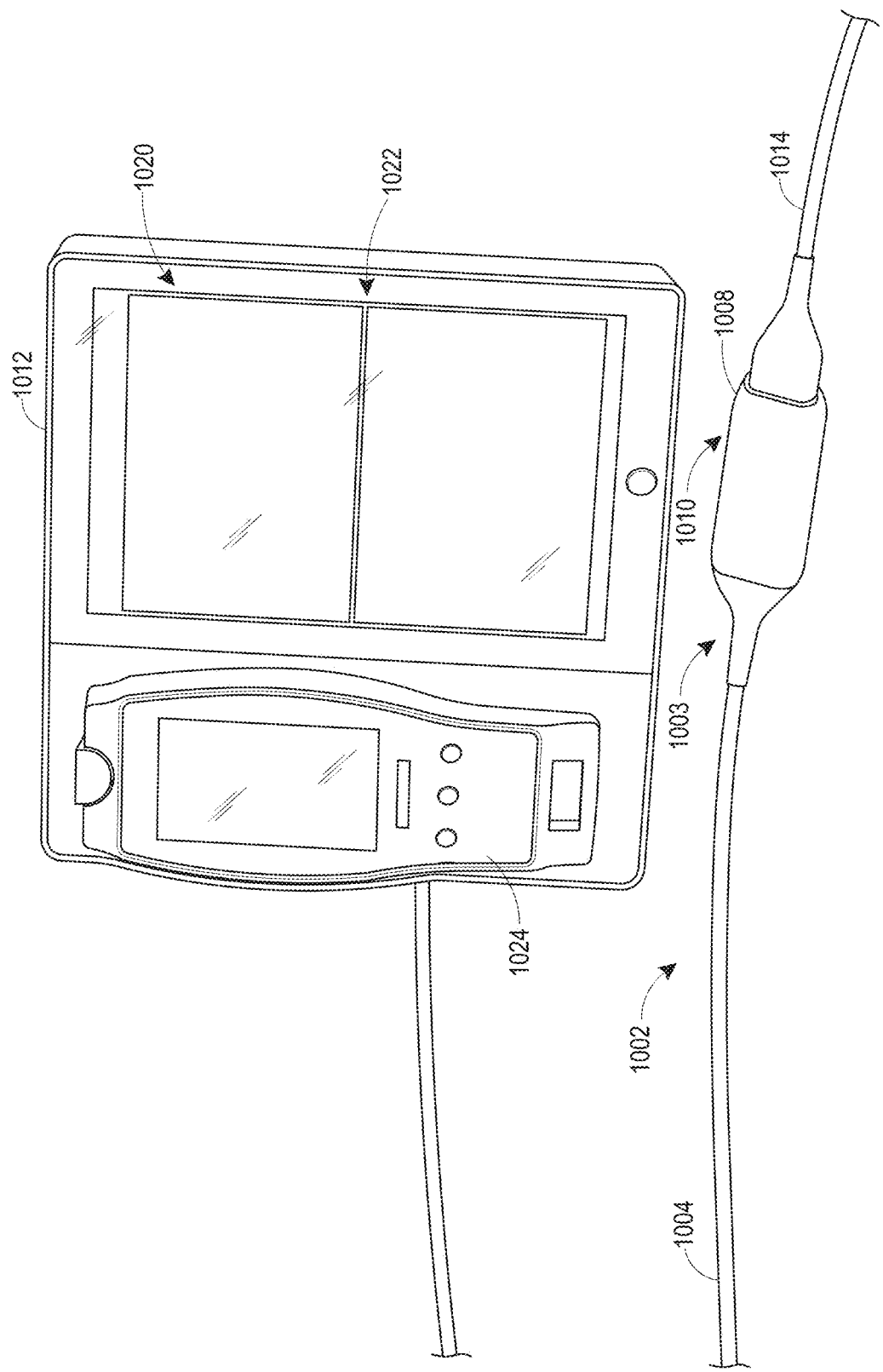
FIG. 11 illustrates one embodiment of the depth of consciousness monitoring system of FIG. 10.

FIG. 11 illustrates another embodiment of a depth of consciousness monitoring assembly 1002 coupled to a multi-parameter monitor (sometimes referred to as a multi-parameter instrument) 1012. The multi-parameter monitor 1012 is configured to receive and display a plurality of physiological parameters received from a patient monitoring device, such as, but not limited to, the depth of consciousness monitoring assembly 1002. The multi-parameter monitor 1012 includes a display 1020. The display 1020 is configured to display a plurality of physiological signals 1022 related to a medical patient. In some embodiments, the display 1020 can be configured to display only selected or groups of physiological signals 1022. In some embodiments, the monitor 1012 can be configured to display a particular view or mode on the display 1020. The view or mode can include one or more pre-selected groupings of physiological signals to display. Examples of different views that may be provided via the display 1020 are discussed below with respect to FIGS. 14-16. Other views, in addition to or instead of those illustrated in FIGS. 14-16 may be displayed on the multi-parameter monitor 1012 display 1020, as well.

In some embodiments, the multi-parameter monitor 1012 also includes a removable module 1024. The removable module 1024 can include a physiological monitor configured to determine one or more physiological parameters associated with the medical patient. For example, in some embodiments, the removable module 1024 includes a respiration rate monitor, a blood oxygen saturation monitor, a blood gas monitor, a carbon monoxide monitor, an ECG monitor, an EKG monitor, a blood pressure monitor, a temperature monitor, a heart rate monitor, etc., or a combination of any one or more of the foregoing.

In the illustrated embodiment of FIG. 11, the depth of consciousness monitor assembly 1002 only includes one cable 1004. A first end of the cable 1004 terminates at a connector (not shown) that is attached to the multi-parameter monitor 1012. The second end of the cable 1003 includes the depth of consciousness processor 1003 and connector 1008, which are integrated within a single housing assembly. The connector end of a sensor 1014 is shown attached to the depth of consciousness monitor assembly's 1002 cable's 1003 second end.

Figure 12:
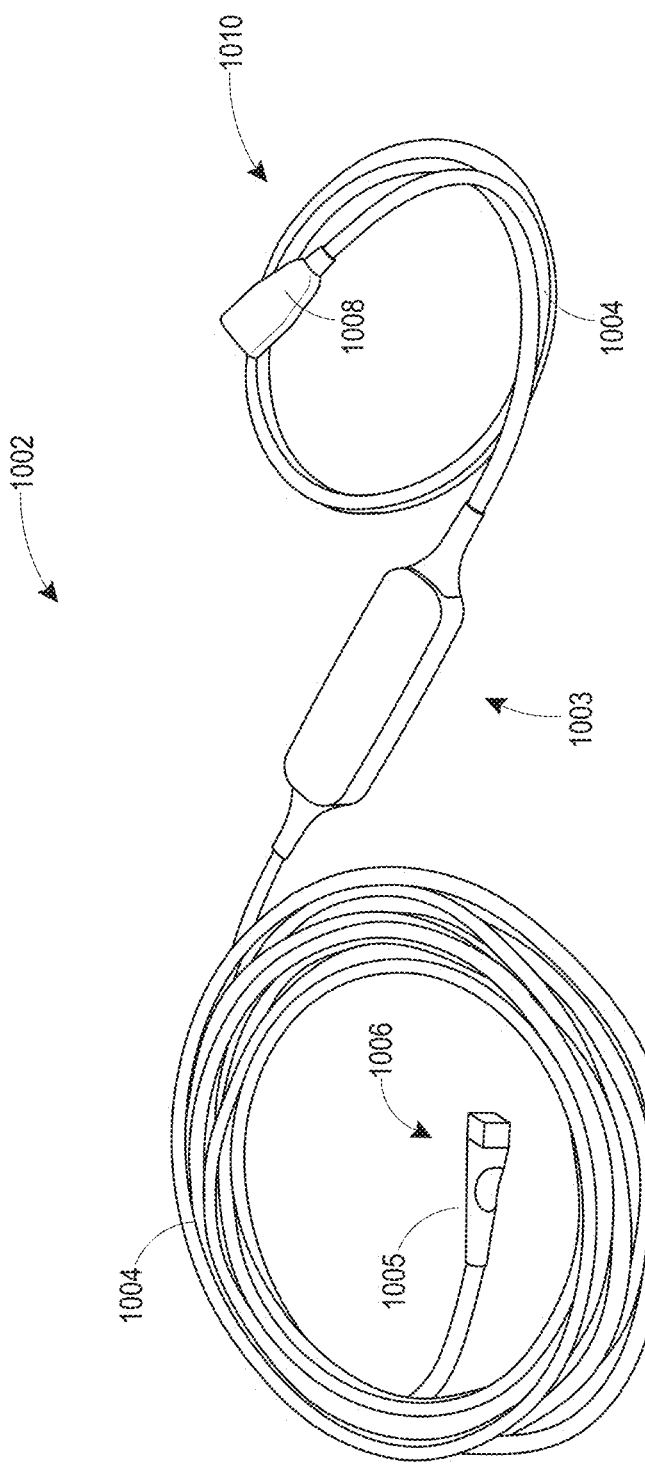
FIG. 12 illustrates one embodiment of the depth of consciousness monitoring assembly of FIG. 10.
Figure 13:
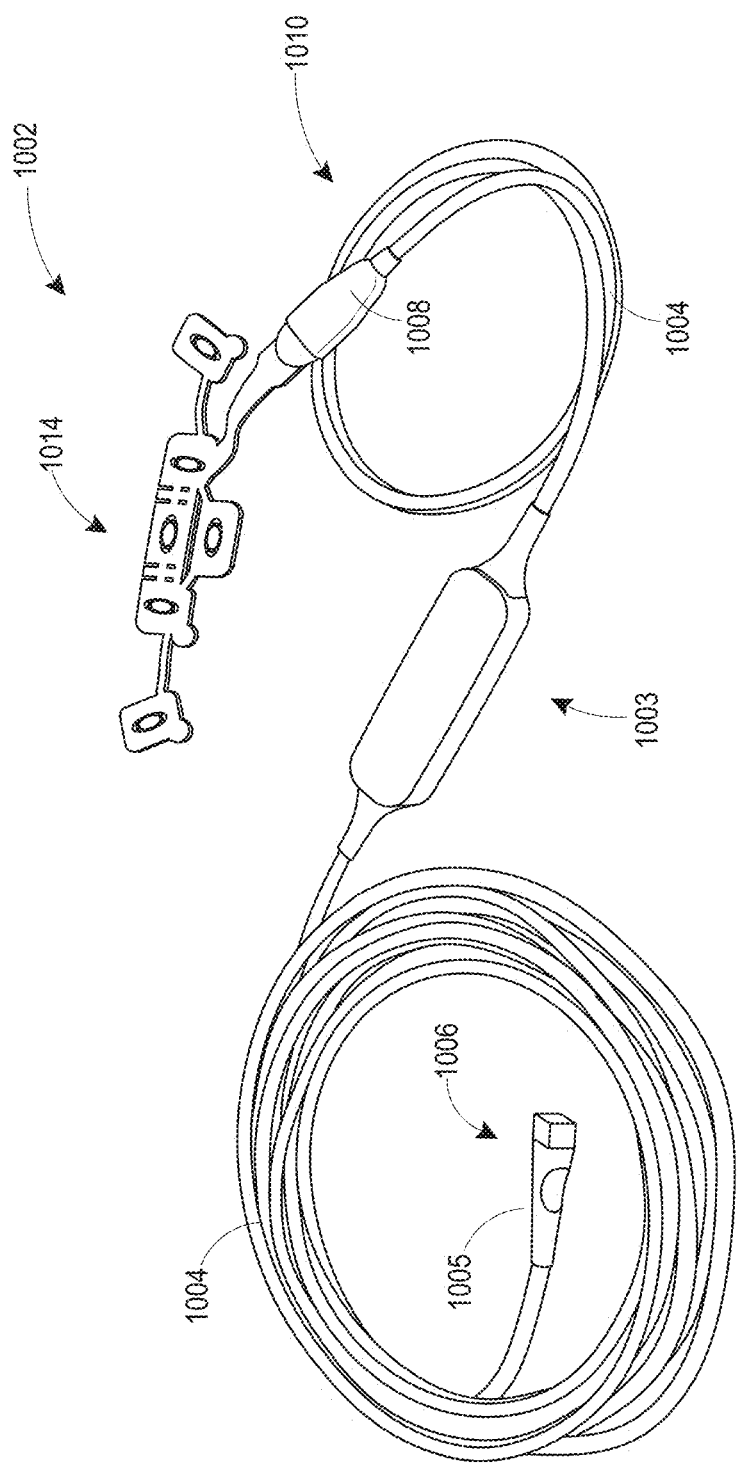
FIG. 13 illustrates the depth of consciousness monitoring assembly of FIG. 12 attached to a sensor assembly.

FIG. 12 illustrates another embodiment of a depth of consciousness monitor assembly 1002. The processor 1003 is positioned between the ends 1006, 1010 of the assembly 1002. The length of the cable 1004 attached to the connector 1008 configured to attach to a sensor (not shown) may be shorter than the length of the cable 1004 attached to the connector 1005 configured to attach to the multi-parameter monitor (not shown). The shorter sensor cable 1004 length can provide additional comfort and less pulling on the sensor when attached to the patient. FIG. 13 illustrates the depth of consciousness monitor assembly 1002 coupled to a sensor 1014. The sensor 1014 can include any of the EEG sensors described above.

Figure 14:
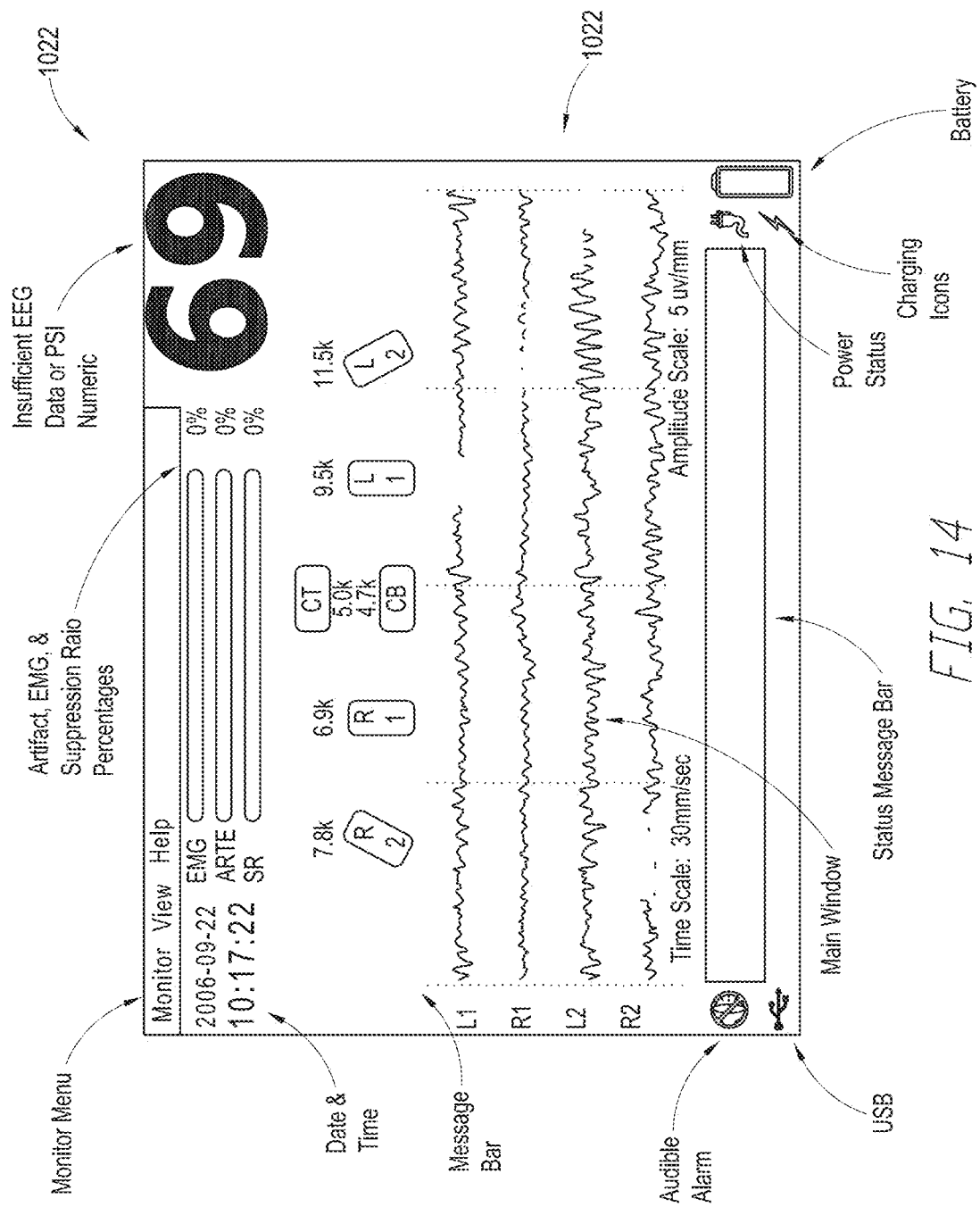
FIGS. 14-16 illustrate views of the display of a multi-parameter monitor displaying physiological signals received from the depth of consciousness monitor of FIG. 10.
Figure 15:
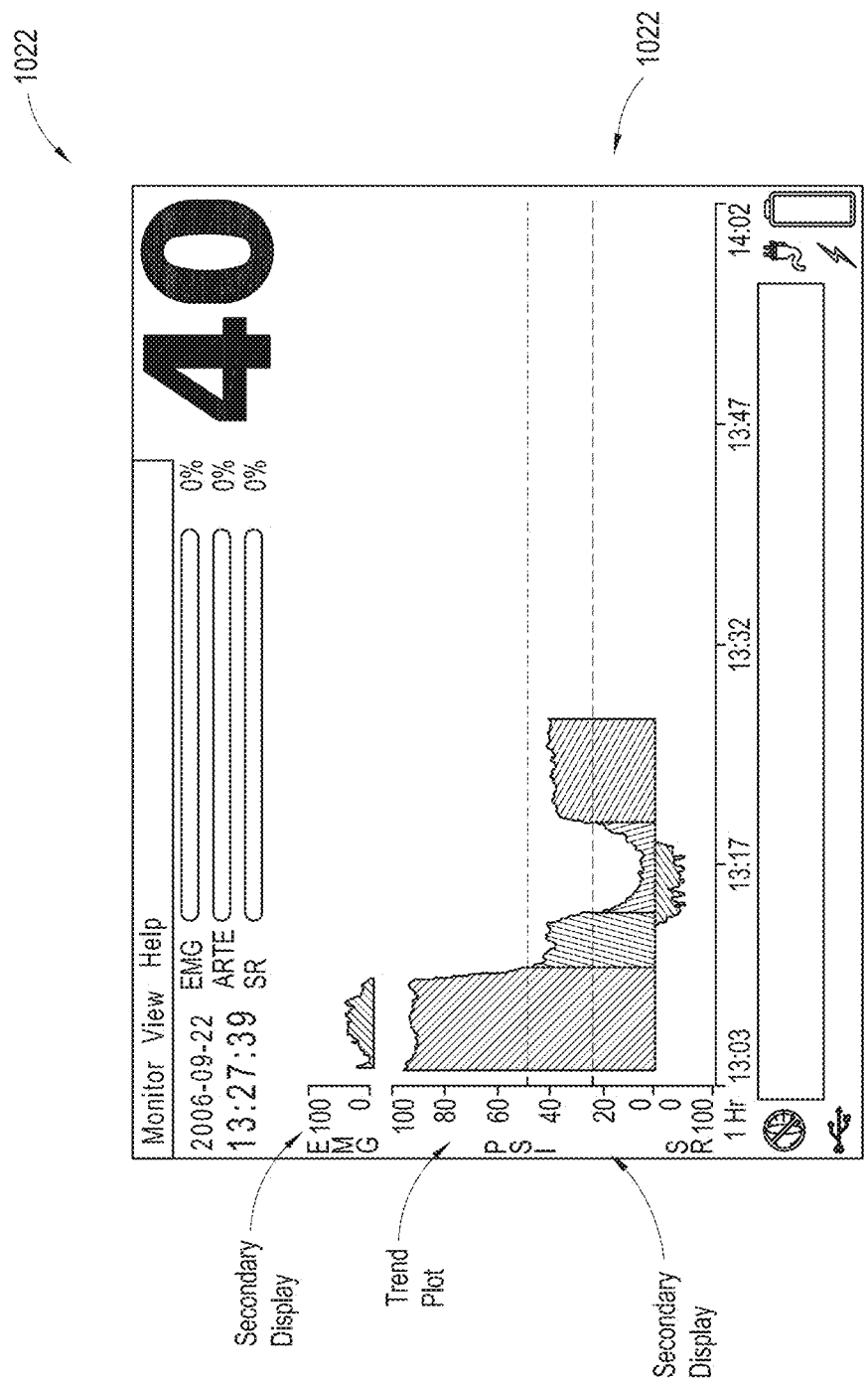
Figure 16:
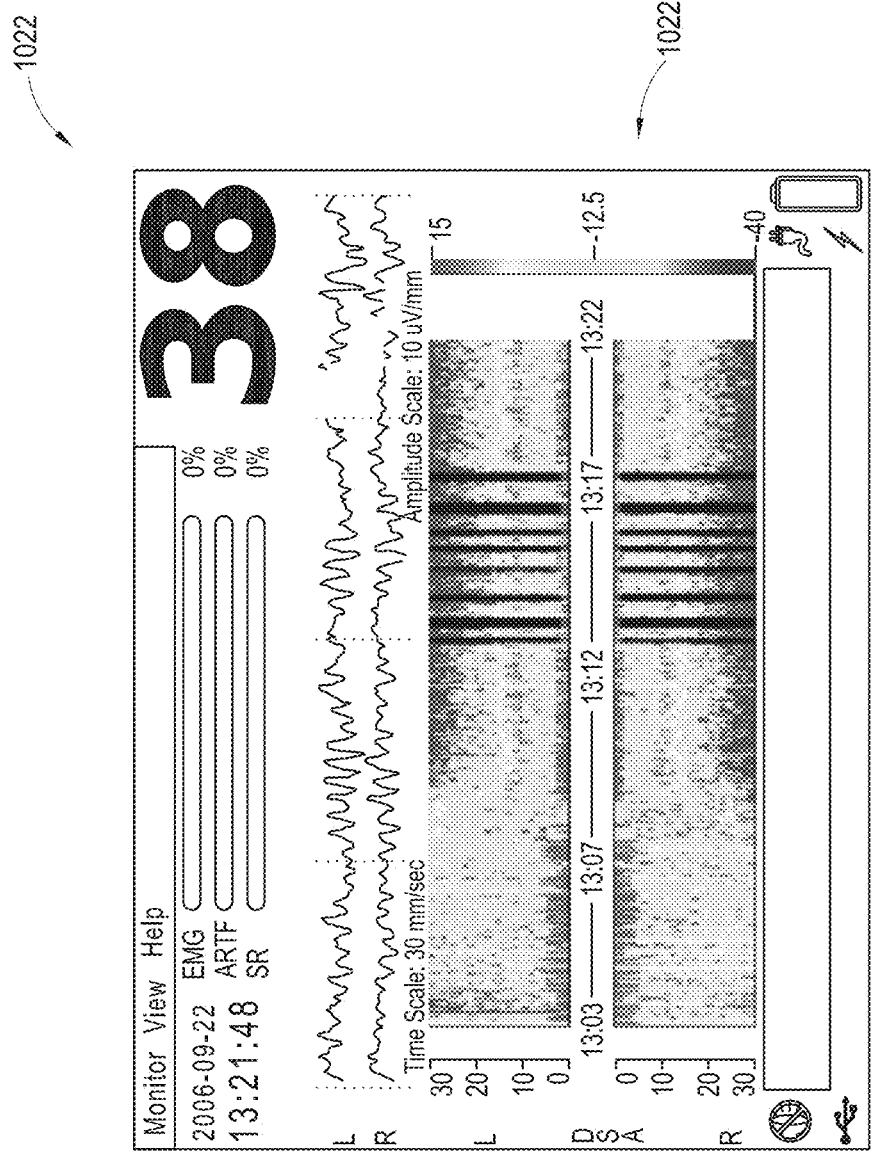

FIGS. 14-16 illustrate views of various parameters 1022 that may be displayed on the multi-parameter monitor 1012 display 1020. The embodiment of FIG. 14 illustrates an EEG view of a multi-parameter monitor 1012. The multi-parameter monitor 1012 view includes a numeric value indicator (e.g., EEG data, insufficient EEG data, patent state index (PSI) value), or any other value described herein, etc.), a bar-graph indicator, menu indicators, date and time indicators, message indicators, physiological waveform indicators, and system status indicators. The physiological waveform indicators can display each of the waveforms received from each electrode (e.g., R2, R1, L1) of an sensor 1014, such as an EEG sensor.

FIG. 15 illustrates a trend view of a multi-parameter monitor 1012. The multi-parameter monitor 1012 view includes a primary indicator or display and a secondary indicator or display. The primary indicator displays the trend of one or more physiological parameters (e.g., PSI, etc.) over time. One or more secondary indicators can display additional physiological parameters of the medical patient, including but not limited to, EMG, and SR. In one embodiment, the secondary indicators display information in the same format (e.g., waveform, solid waveform, bargraph, etc.) as the primary (e.g., trend plot) indicator, but at a smaller size. In other embodiments, the secondary indicators display information in a different format than the primary (e.g., trend plot, etc.) indicator. FIG. 16 illustrates a density spectral array view of a multi-parameter monitor 1012. The multi-parameter monitor 1012 view includes a spectral density indicator Each of the displayed physiological parameters can be determined by the depth of consciousness processor 1003. In addition, the multi-parameter monitor 1012 can be configured to display any one or more of the parameters discussed above, as well as other parameters, such as signals from the removable module 1024, when provided.

All publications, patents, and patent applications mentioned in this specification are herein incorporated by reference to the same extent as if each individual publication, patent, or patent application was specifically and individually indicated to be incorporated by reference.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The steps of a method, process, routine, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An example storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A depth of consciousness monitor configured to determine a level of sedation of a medical patient, the depth of consciousness monitor comprising:

an EEG interface configured to receive an EEG signal from an EEG sensor;

an EEG front end configured to pre-process the EEG signal, wherein the EEG signal is assigned a first time stamp;

a processor, configured to determine the level of sedation of the medical patient based at least upon the pre-processed EEG signal, the processor comprising:

two or more parallel computing engines, each configured to receive as an input a same first time stamped pre-processed EEG signal and compute a possible sedation level according to a different processing approach, each processing approach configured to simultaneously calculate the possible sedation level using the same first time stamped pre-processed EEG signal; and a decision logic module, configured to arbitrate the possible sedation level computations as computed by the two or more parallel computing engines on the same first time stamped pre-processed EEG signal and based on the arbitration, determine a patient sedation index corresponding to an estimated level of sedation of the medical patient, wherein the arbitration comprises selecting a subset of possible sedation levels generated by the two or more parallel compute engines, wherein the arbitration is based at least on data associated with at least one sedation drug acting on the medical patient and the selected subset of possible sedation levels generated by the two or more parallel compute engines; and a data port configured to transmit the level of sedation of the medical patient.

2. The depth of consciousness monitor of claim 1, wherein the data port comprises a multi-parameter physiological monitor interface configured to receive power from a multi-parameter physiological monitor and provide at least the level of sedation of the medical patient to the multi-parameter physiological monitor.

3. The depth of consciousness monitor of claim 1, wherein at least one of the computing engines is configured to implement a motion vector process to compute one of the possible sedation levels.

4. The depth of consciousness monitor of claim 1, wherein at least one of the computing engines is configured to implement a phase coherence process to compute one of the possible sedation levels.

5. The depth of consciousness monitor of claim 1, wherein at least one of the computing engines is configured to utilize a brain model to compute one of the possible sedation levels.

6. The depth of consciousness monitor of claim 1, wherein the EEG front end comprises an EEG engine and an EMG engine configured to extract EEG information and EMG information from the EEG signal, respectively.

7. The depth of consciousness monitor of claim 1, wherein the data port comprises a display.

8. The depth of consciousness monitor of claim 1, wherein the data port comprises a wireless communication device.

* * * * *